United States Patent
Cistola

(10) Patent No.: US 12,429,544 B2
(45) Date of Patent: Sep. 30, 2025

(54) METHOD AND DEVICE FOR DETECTING SUBCLINICAL HYPOXEMIA USING WHOLE BLOOD $T_{2P}$

(71) Applicant: Texas Tech University System, Lubbock, TX (US)

(72) Inventor: David P. Cistola, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 18/608,144

(22) Filed: Mar. 18, 2024

(65) Prior Publication Data

US 2024/0310465 A1 Sep. 19, 2024

Related U.S. Application Data

(60) Provisional application No. 63/452,984, filed on Mar. 17, 2023.

(51) Int. Cl.
*G01R 33/50* (2006.01)
*G01N 33/49* (2006.01)
(Continued)

(52) U.S. Cl.
CPC ......... *G01R 33/50* (2013.01); *G01N 33/4925* (2013.01); *G01N 33/726* (2013.01); *G01R 33/465* (2013.01)

(58) Field of Classification Search
CPC .. G01R 33/465; G01R 33/50; G01N 33/4925; G01N 33/726
(Continued)

(56) References Cited

U.S. PATENT DOCUMENTS 7,715,901 B2 * 5/2010 Salomon ............ G01R 33/4806
424/9.4
10,429,467 B2 * 10/2019 Peng ...................... G01R 33/50
(Continued)

FOREIGN PATENT DOCUMENTS

WO WO-2016176668 A1 * 11/2016 ......... A61B 5/14542

OTHER PUBLICATIONS

Chien et al.; "MR Gradient Echo Imaging of Intravascular Blood Oxygenation: T2* Determination in the Presence of Flow"; Aug. 1994; Magnetic resonance in medicine; 32.4; pp. 540-545 (Year: 1994).*
(Continued)

*Primary Examiner* — Eman A Alkafawi
*Assistant Examiner* — Rahul Maini
(74) *Attorney, Agent, or Firm* — Shackelford, McKinley & Norton, LLP

(57) ABSTRACT

The present disclosure pertain to methods of detecting hypoxemia in a subject by: (1) receiving a blood sample from the subject; (2) measuring the $T_2$ relaxation time constant of the blood cell (e.g., blood cell pellet) of the blood sample ($T_{2P}$ value); and (3) correlating the measured $T_{2P}$ value to hypoxemia. The methods of the present disclosure also include a step of correlating the measured $T_{2P}$ value to the subject's susceptibility to one or more hypoxemia-related conditions. The present disclosure also pertains to systems for detecting hypoxemia in a subject in accordance with the methods of the present disclosure.

21 Claims, 12 Drawing Sheets

(51) Int. Cl.
  *G01N 33/72* (2006.01)
  *G01R 33/465* (2006.01)
(58) Field of Classification Search
  USPC .......................................................... 324/309
  See application file for complete search history.

(56) References Cited

U.S. PATENT DOCUMENTS

| | | | |
|---|---|---|---|
| 2004/0057940 | A1 | 3/2004 | Kim et al. |
| 2006/0011199 | A1* | 1/2006 | Rashad ............. A61M 16/0677 128/204.23 |
| 2011/0059475 | A1 | 3/2011 | May et al. |
| 2013/0214779 | A1* | 8/2013 | Tietjen ..................... G01V 3/38 324/303 |
| 2017/0224259 | A1* | 8/2017 | Simonetti .............. G01R 33/50 |
| 2018/0113141 | A1 | 4/2018 | Lowery, Jr. et al. |
| 2019/0247010 | A1 | 8/2019 | Barnacka et al. |
| 2022/0142530 | A1* | 5/2022 | Lim .................... A61B 5/14551 |
| 2023/0056088 | A1* | 2/2023 | Crawley ................ G01R 33/50 |

OTHER PUBLICATIONS

Choi et al.; "Effects of chemical modification of wheat starch on molecular mobility as studied by pulsed 1H NMR"; Pub. Date Oct. 2, 2002; LWT—Food Science and Technology; vol. 36.1; pp. 105-112 (Year: 2002).*
Cosinuss; "Oxygen Saturation"; webpage https://www.cosinuss.com/en/measured-data/vital-signs/oxygen-saturation/; 1 page; Apr. 11, 2021; retrieved from Internet Archive Wayback Machine (Year: 2021).*
Cleveland; "Blood Oxygen Level"; webpage https://my.clevelandclinic.org/health/diagnostics/22447-blood-oxygen-level; 14 pages; Apr. 19, 2022; retrieved from Internet Archive Wayback Machine (Year: 2022).*
Thulborn et al.; Oxygenation Dependence of the Transverse Relaxation Time of Water Protons in Whole Blood at High Field; Feb. 1982; Biochimica et Biophysica Acta; 714; pp. 265-270 (Year: 1982).*
Robinson MD, Deodhar S, Mishra I, et al. Water as a Universal Biosensor for Inflammation, Insulin Resistance and Dyslipidemia. Arterioscler Thromb Vasc Biol. 2015;35:A620.
Boyle JP, Honeycutt AA, Narayan KM, et al. Projection of diabetes burden through 2050: impact of changing demography and disease prevalence in the U.S. Diabetes Care. 2001;24(11):1936-1940.
Mishra I, Jones C, Patel V, Deodhar S, Cistola DP. Early detection of metabolic dysregulation using water T2 analysis of biobanked samples. Diabetes Metab Syndr Obes. Nov. 23, 2018;11:807-818. doi: 10.2147/DMSO.S180655. PMID: 30538517; PMCID: PMC6260129.
Patel V, Dwivedi AK, Deodhar S, Mishra I, Cistola DP. Aptamer-based search for correlates of plasma and serum water T2: implications for early metabolic dysregulation and metabolic syndrome. Biomark Res. Sep. 17, 2018;6:28. doi: 10.1186/s40364-018-0143-x. PMID: 30237882; PMCID: PMC6142358.
Sandoval et al.,Abstract EP05: Plasma Water T2 Is a Global Marker of Cardiometabolic Health: The Premier Study, Apr. 7, 2022, https://doi.org/10.1161/circ.145.suppl_1.EP05Circulation. 2022;145:AEP05.
Nicasio et al., Abstract EP06: Serum Water T and Its Association With Cardiometabolic Health: The Premier Study; Apr. 7, 2022 https://doi.org/10.1161/circ.145.suppl_1.EP06 Circulation. 2022; 145:AEP06.
Robinson MD, Mishra I, Deodhar S, et al. Water T2 as an early, global and practical biomarker for metabolic syndrome: an observational cross-sectional study. J Transl Med. 2017;15(1):25-5.
Matthews DR, Hosker JP, Rudenski AS, Naylor BA, Treacher DF, Turner RC. Homeostasis model assessment: insulin resistance and beta-cell function from fasting plasma glucose and insulin concentrations in man. Diabetologia. 1985;28(7):412-419.
McAuley KA, Williams SM, Mann JI, et al. Diagnosing insulin resistance in the general population. Diabetes Care. 2001;24(3):460-464.
David P. Cistola, Vipulkumar Patel, Sneha Deodhar, Ina Mishra, Michelle D. Robinson, Alok K. Dwivedi, Whole Blood T2P Links Hemoglobin Status to Cardiometabolic Health, American Journal of Preventive Cardiology, vol. 15, Supplement, 2023.
Cistola DP, Robinson MD. Compact NMR relaxometry of human blood and blood components. Trends Analyt Chem. Nov. 2016;83(A):53-64. doi: 10.1016/j.trac.2016.04.020. PMID: 28003711; PMCID: PMC5167358.
Cistola & Dwivedi, Abstract P336: Early Metabolic Imbalance in Young Adults is a Hidden Risk Factor for Midlife Cardiovascular Disease: Cardia 35-year Follow Up; Mar. 14, 2023 https://doi.org/10.1161/circ.147.suppl_1.P336 Circulation. 2023; 147:AP336.
Bradley et al., High Prevalence of Compensatory Hyperinsulinemia in U.S. Teenagers: The 2015-2018 National Health and Nutrition Examination Survey (NHANES)Metabolism vol. 128, Supplement, Mar. 2022.
Pan XR, Li GW, Hu YH, et al. Effects of diet and exercise in preventing NIDDM in people with impaired glucose tolerance. The Da Qing IGT and Diabetes Study. Diabetes Care. 1997;20(4):537-544.
Knowler WC, Barrett-Connor E, Fowler SE, et al. Reduction in the incidence of type 2 diabetes with lifestyle intervention or metformin. N Engl J Med. 2002;346(6):393-403.
Tuomilehto J, Lindstrom J, Eriksson JG, et al. Prevention of Type 2 Diabetes Mellitus by Changes in Lifestyle among Subjects with Impaired Glucose Tolerance. N Engl J Med. 2001;344(18):1343-1350.
Abdul-Ghani MA, Tripathy D, DeFronzo RA. Contributions of beta-cell dysfunction and insulin resistance to the pathogenesis of impaired glucose tolerance and impaired fasting glucose. Diabetes Care. 2006;29(5):1130-1139.
Ahn CW, Kim CS, Nam JH, et al. Effects of growth hormone on insulin resistance and atherosclerotic risk factors in obese type 2 diabetic patients with poor glycaemic control. Clin Endocrinol (Oxf). 2006;64(4):444-449.
Fernandez-Real JM, Ricart W. Insulin resistance and chronic cardiovascular inflammatory syndrome. Endocr Rev. 2003;24(3):278-301.
Luo Z, Fox L, Cummings M, Lowery TJ, Daviso E. New frontiers in in vitro medical diagnostics by low field T2 magnetic resonance relaxometry. TrAC Trends in Analytical Chemistry. 2016.
Spees WM, Yablonskiy DA, Oswood MC, Ackerman JJH. Water proton MR properties of human blood at 1.5 Tesla: Magnetic susceptibility, T1, T2, T?*2, and non-Lorentzian signal behavior. Magnetic Resonance in Medicine. 2001;45(4):533-542.
International Search Report for PCT/US2024/020371, mailed on Jul. 1, 2024.

* cited by examiner

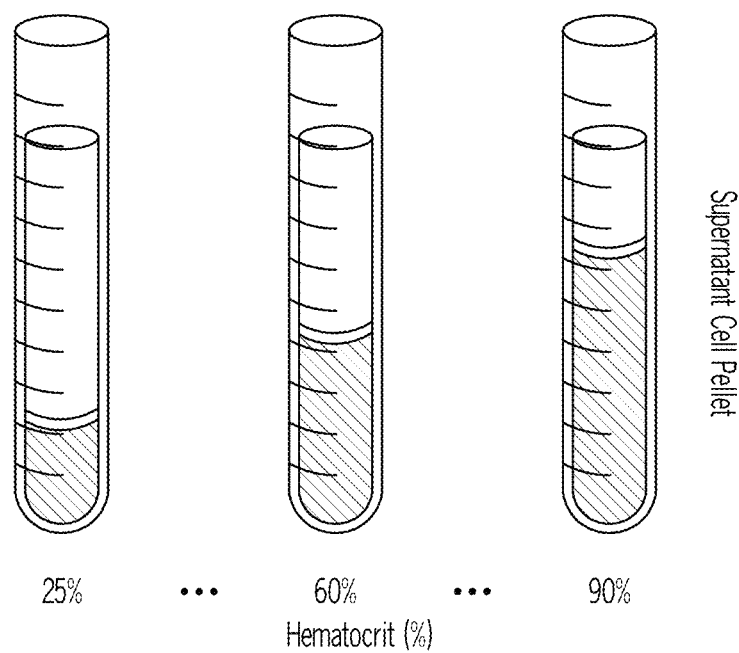
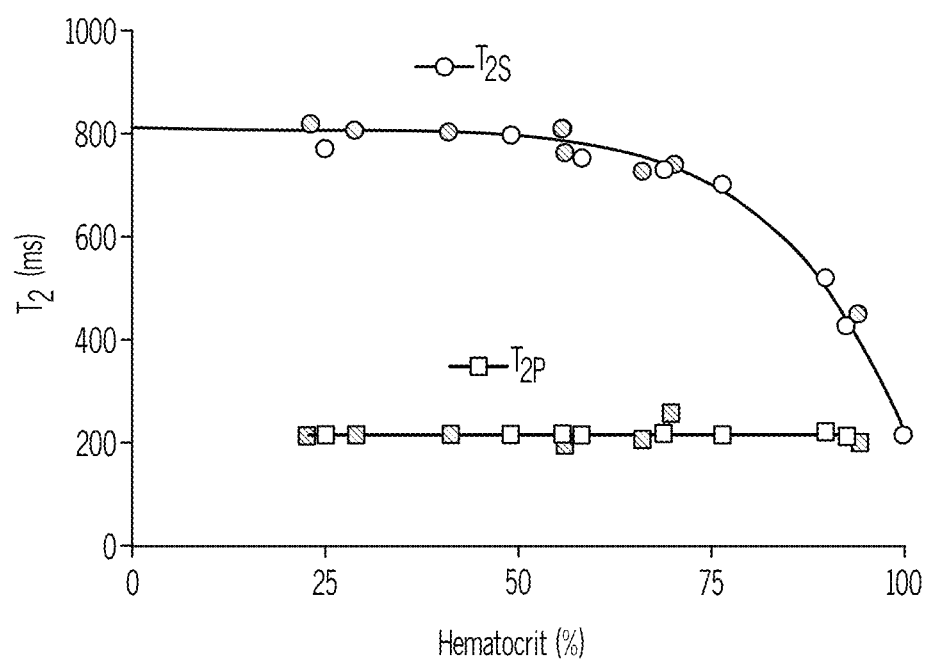
FIG. 6 chronic hyperinsulinemia: ↑↑ insulin & c-peptide
overstimulates eNOS: ↑↑ NO

⇩ oxidative stress chronic subclinical met-hemoglobinemia: ↓ $T_2p$
↓$O_2$ binding capacity of Hb: subclinical hypoxemia
<u>not</u> detected by pulse oximetry ⇩ ↓$O_2$ delivery cell/tissue hypoxia: ↑ lactate, uric acid
chronic inflammation: ↑ IgG, hs-CRP
cell/tissue damage: liver, adipose, heart, β-cells (?)

FIG. 9

Linked regression equations of the form:

$$Y = a_0 + \beta_1 X_1 + \beta_2 X_2 + \beta_3 X_3$$

O = outcome variable (lactate or IgG)
E = exposure variable (insulin or c-peptide)
M = mediating variable ($T_2p$)
c = confounding variables (age, sex)

| | | | |
|---|---|---|---|
| Eq 1: | O = E + c | lactate = insulin + c | p=0.0044 |
| Eq 2: | O = M + c | lactate = $T_2p$ + c | p=0.0007 |
| Eq 3: | E = M + c | insulin = $T_2p$ + c | p=0.0018 |
| Eq 4: | O = E + M + c | lactate = insulin + $T_2p$ + c | |
| | | p=0.1039  p=0.0154 | |

$T_2p$ is a full mediator of the association between insulin and lactate
(similar results for c-peptide & lactate, insulin & IgG, c-peptide & IgG )

FIG. 10

METHOD AND DEVICE FOR DETECTING SUBCLINICAL HYPOXEMIA USING WHOLE BLOOD $T_{2P}$

CROSS-REFERENCE TO RELATED APPLICATIONS

This application claims priority to U.S. Provisional Patent Application No. 63/452,984, filed on Mar. 17, 2023. The entirety of the aforementioned patent application is incorporated herein by reference.

BACKGROUND

A need exists for more sensitive and readily accessible screening tools for detecting hypoxemia, especially subclinical hypoxemia. Numerous embodiments of the present disclosure aim to address the aforementioned need.

SUMMARY

In some embodiments, the present disclosure pertains to methods of detecting hypoxemia in a subject by: (1) receiving a blood sample from the subject; (2) measuring the $T_2$ relaxation time constant of the blood cell of a blood sample (e.g., blood cell pellet of a settled, anti-coagulated whole blood sample) ($T_{2P}$ value); and (3) correlating the measured $T_{2P}$ value to hypoxemia. In some embodiments, the methods of the present disclosure also include a step of correlating the measured $T_{2P}$ value to the subject's susceptibility to one or more hypoxemia-related conditions. In some embodiments, the methods of the present disclosure also include a step of making a treatment decision, such as monitoring the subject and/or administering a therapeutic agent and/or intervention to the subject. In some embodiments, the methods of the present disclosure are repeated after implementing the treatment decision.

Additional embodiments of the present disclosure pertain to systems for detecting hypoxemia in a subject. In some embodiments, the systems of the present disclosure include one or more computer-readable storage mediums having a program code embodied therewith. In some embodiments, the program code includes programming instructions for: (1) receiving a blood sample from the subject; (3) measuring the $T_2$ relaxation time constant of blood cells of the blood sample ($T_{2P}$ value); and (4) correlating the measured $T_{2P}$ value to hypoxemia. In some embodiments, the systems of the present disclosure also include programming instructions for correlating the measured $T_{2P}$ value to the subject's susceptibility to one or more hypoxemia-related conditions. In some embodiments, the systems of the present disclosure also include programming instructions for recommending a treatment decision. In some embodiments, the systems of the present disclosure also include programming instructions for repeating the programming instructions after the implementation of the treatment decision.

Additional embodiments of the present disclosure pertain to magnetic resonance devices. In some embodiments, the magnetic resonance device is optimized for measuring whole blood $T_{2P}$ values.

DESCRIPTION OF THE DRAWINGS

FIG. 2A shows the raw CPMG decay curve acquired from a sample of settled, whole human blood using the CPMG pulse sequence. FIG. 2B shows the $T_2$ profile obtained from an inverse Laplace transformation (ILT) of the decay curve using the CONTIN algorithm. The X-axes in both the decay curve and ILT are time and $T_2$, respectively, in milliseconds.

FIG. 6 shows the effect of hematocrit on $T_{2S}$ and $T_{2P}$, showing the $r^{-6}$ distance dependence of $T_{2S}$ on hematocrit arising from paramagnetic relaxation enhancement. As the relative height of the plasma supernatant decreases as the hematocrit increases (top right), the plasma water molecules are, on average, located closer to the paramagnetic cell pellet. Thus, they are affected more by paramagnetic relaxation enhancement, lowering $T_{2S}$. In this ex vivo experiment, the non-physiological high and low values of hematocrit were achieved by removing or adding plasma to the whole blood sample, respectively.

FIG. 9 illustrates a hypothetical mechanistic link whereby hemoglobin oxidation (subclinical met-hemoglobinemia) mediates the association between hyperinsulinemia and downstream hypoxia and chronic inflammation.

FIG. 10 shows causal mediation analysis to test the hypothesis in FIG. 9, using four (4) linked regression equations.

FIG. 13A shows a Bruker mq20 benchtop time-domain NMR relaxometry instrument operating at 0.47 Tesla (20 MHz for proton). FIG. 13B shows a Resonance Systems benchtop NMR time-domain relaxometry instrument operating at 0.5 Tesla (23 MHz for proton). FIG. 13C shows a Waveguide Corporation miniaturized portable time-domain relaxometry device operating at 0.47 Tesla (20 MHz for proton).

DETAILED DESCRIPTION

Figure 1A:
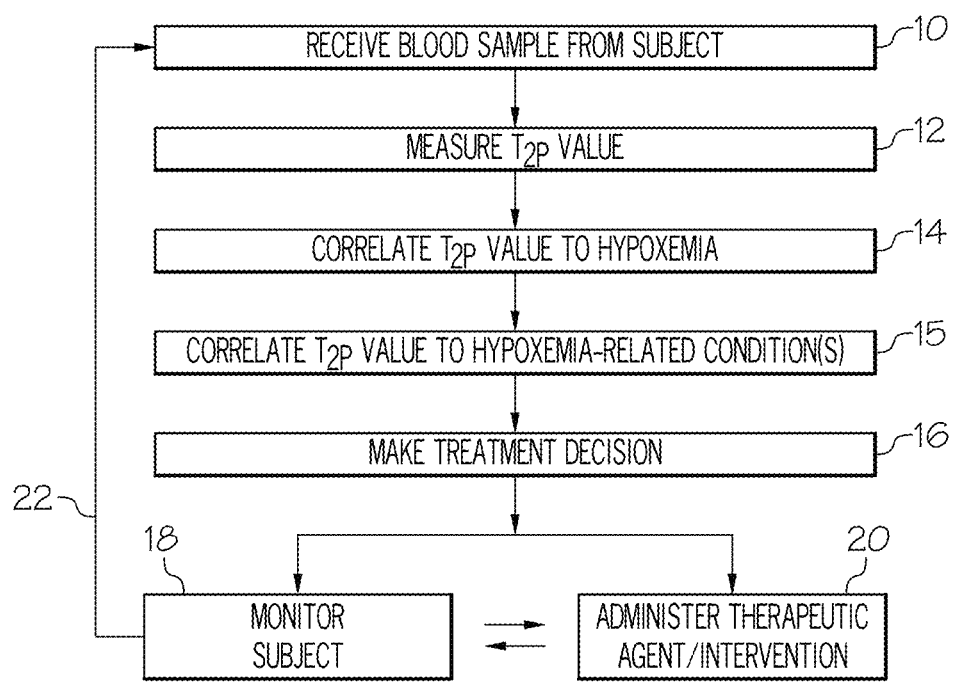
FIG. 1A illustrates a method of detecting hypoxemia in a subject.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials define a term in a manner that contradicts the definition of that term in this application, this application controls.

Hypoxemia refers to decreased levels of oxygen in the blood and is typically caused by blocked airways or serious lung, heart or blood diseases. Specific examples are the hypoxemia that occurs in patients with chronic obstructive pulmonary disease (COPD) or in hospitalized patients with COVID-19. In critical care units, the patient's blood oxygen levels are monitored using a combination of pulse oximetry and arterial blood gas analysis.

In contrast with the overt clinical hypoxemia seen in sick patients, a more subtle hidden condition (subclinical hypoxemia) can occur in apparently healthy individuals. The impact of subclinical hypoxemia depends on its intensity and duration, and on the body's ability to compensate for it, both acutely and chronically.

Thus, subclinical hypoxemia does not necessarily mean that cells and tissues are being deprived of oxygen (hypoxia). In fact, subclinical hypoxemia is an under-recognized condition, even though many patients undergoing a wellness exam in a medical office are screened for oxygen saturation using a fingertip pulse oximeter.

Pulse oximetry is a helpful tool for detecting undiagnosed clinical hypoxemia (e.g., undiagnosed lung, heart, blood or airway disease). A resting oxygen saturation from pulse oximetry ($SpO_2$) below ~95% at sea level during routine screening would alert the clinician to the possibility of a medical problem and would prompt further evaluation.

However, subtle subclinical hypoxemia is more difficult to detect, as there is no consensus in the medical literature on what constitutes a normal $SpO_2$ level. For example, a resting $SpO_2$ of 95% in one patient may be normal. By contrast, a resting $SpO_2$ of 95% in a different patient would be abnormal if that patient previously had a $SpO_2$ of 98% under the same conditions. Thus, subtle decreases in the percent of hemoglobin oxygen saturation can elude detection by fingertip pulse oximetry.

Moreover, pulse oximeters do not detect oxidized hemoglobin, also known as methemoglobin or MetHb. Such a limitation is significant because MetHb is non-functional (i.e., it cannot bind and deliver oxygen to the tissues). Levels of MetHb above ~20% of total hemoglobin produce overt symptoms of hypoxemia while levels above 50% are life-threatening or fatal.

The body has reductase enzymes to convert oxidized MetHb back to reduced, functional Hb. Under normal conditions, these reductases keep the MetHb level in the blood low (i.e., ~1% on average). However, the reductase system may become overwhelmed under conditions of acute or chronic oxidative stress.

One possible source of oxidative stress is hyperinsulinemia (i.e., high levels of fasting insulin in the blood of individuals with early insulin resistance). Normally, insulin increases the production of nitric oxide, a potent vasodilator that increases blood flow to tissues to aid in nutrient delivery following a meal. However, abnormal chronic elevations in insulin and nitric oxide can lead to oxidative stress, as nitric oxide is a pro-oxidant. To alleviate that stress, the body reduces nitric oxide at the cost of oxidizing hemoglobin and generating more MetHb. In this way, hidden metabolic imbalances could lead to undetected subclinical hypoxemia in apparently healthy individuals.

Over time, subclinical hypoxemia may slowly deprive cells and tissues of oxygen, thereby damaging the beta cells of the pancreas and the inner walls of arteries. Slow loss of beta cells leads to type 2 diabetes, and the progressive blockage of arteries leads to heart disease and stroke.

As such, untreated subclinical hypoxemia can have various health repercussions, such as the onset of diabetes. The diabetes pandemic is a major threat to the health and well-being of many societies. For instance, approximately 14% of the US adult population has diagnosed or undiagnosed diabetes, and the prevalence is projected to double by 2050. The best strategy for altering this trend is to prevent or delay the onset of disease.

Evidence-based prevention programs for type 2 diabetes rely on fasting glucose, hemoglobin A1c (glycated hemoglobin) and/or glucose tolerance tests to identify individuals at increased risk. However, by the time an individual develops glucose intolerance, a 50-70% decline in pancreatic insulin secretory capacity has already occurred. Moreover, glucose and $Hb_{A1c}$ fail to identify early metabolic imbalance, which includes compensated insulin resistance, oxidative stress and inflammation, with subclinical alterations in proteins and lipoproteins in the blood.

Arterial blood gas analysis can be used to detect subclinical abnormalities of hemoglobin, including decreased oxygen saturation and increased oxidized hemoglobin. However, arterial blood gas analysis is expensive and invasive. As such, arterial blood gas analysis is typically used only in critical care units and emergency departments, thereby making the analysis impractical for routine health screening in outpatient clinics.

Accordingly, a need exists for more sensitive and readily accessible screening tools for detecting markers of cardio-metabolic health. Numerous embodiments of the present disclosure aim to address the aforementioned need.

In some embodiments, the present disclosure pertains to methods of detecting hypoxemia in a subject. In some embodiments illustrated in FIG. 1A, the methods of the present disclosure include: receiving a blood sample from the subject (step 10); measuring the $T_2$ relaxation time constant of the blood cells of the blood sample (e.g., the $T_2$ relaxation time constant of the blood cell pellet in an anticoagulated sample of settled whole blood) ($T_{2P}$ value) (step 12); and correlating the measured $T_{2P}$ value to hypoxemia (step 14). In some embodiments, the methods of the present disclosure also include a step of correlating the measured $T_{2P}$ value to the subject's susceptibility to one or more hypoxemia-related conditions (step 15). In some embodiments, the methods of the present disclosure also include a step of making a treatment decision (step 16), such as monitoring the subject (step 18) and/or administering a therapeutic agent and/or intervention to the subject (step 20). In some embodiments, the methods of the present disclosure are repeated after implementing the treatment decision (step 22).

In some embodiments, the present disclosure pertains to systems for detecting hypoxemia in a subject. In some embodiments, the systems of the present disclosure include one or more computer-readable storage mediums having a program code embodied therewith. In some embodiments, the program code includes programming instructions for: receiving a blood sample from the subject; measuring the $T_2$ relaxation time constant of blood cells of the blood sample ($T_{2P}$ value); and correlating the measured $T_{2P}$ value to hypoxemia. In some embodiments, the systems of the present disclosure also include programming instructions for correlating the measured $T_{2P}$ value to the subject's susceptibility to one or more hypoxemia-related conditions. In some embodiments, the systems of the present disclosure also include programming instructions for recommending a treatment decision. In some embodiments, the systems of the present disclosure also include programming instructions for repeating the programming instructions after the implementation of the treatment decision.

As set forth in more detail herein, the methods and systems of the present disclosure can have numerous embodiments.

Blood Samples

The methods and systems of the present may evaluate various types of blood samples. For instance, in some embodiments, the blood sample includes a whole blood sample. In some embodiments, the whole blood sample contains an anti-coagulant to prevent the blood from clotting.

In some embodiments, the blood sample includes a blood cell component of the blood sample. In some embodiments, the blood cell component includes red blood cells, white blood cells, and platelets. In some embodiments, the blood cell component is mostly comprised of red blood cells, but also white blood cells and platelets.

In some embodiments, the blood cell component is in the form of a pellet. In some embodiments, the pelleted blood cell component is settled or separated from the liquid plasma (i.e., the non-cellular liquid component of the blood) in an anti-coagulated sample of whole blood. In some embodiments, the pelleted blood cell component is in the form of a separated pellet formed by centrifuging the sample, or by spontaneous settling of the cells to the bottom of the tube. In some embodiments, such a process separates the cells from the supernatant plasma. In some embodiments, the settled or separated blood cell component of the blood sample is in anti-coagulated form.

In some embodiments, the blood cell component is in the form of a pellet of an anti-coagulated whole blood sample.

In some embodiments, the blood cell pellet represents a settled and anti-coagulated whole blood sample.

In some embodiments, the blood cell component is purified and isolated from the plasma. In some embodiments, the red blood cell component is purified and isolated from the white blood cell, platelet and plasma components. In some embodiments, the blood sample includes a pelleted blood cell component that is settled or separated from the liquid plasma in an anti-coagulated sample of whole blood.

In some embodiments, the methods of the present disclosure also include a step of obtaining a blood sample from a subject. For instance, in some embodiments, a blood sample is obtained from a subject through venipuncture. In some embodiments, a blood sample is obtained from a subject through a fingerstick drop or an upper arm blood collection device equipped with a microtainer tube.

$T_{2P}$ Values

The methods and systems of the present disclosure may measure various $T_{2P}$ values in various manners. For instance, in some embodiments, the $T_{2P}$ value represents the spin-spin relaxation time constant of the whole blood sample. In some embodiments, the $T_{2P}$ value represents the spin-spin relaxation time constant of the settled or separated blood cell component of the blood sample. In some embodiments, the settled or separated blood cell component of the blood sample is in anti-coagulated form. In some embodiments, the $T_{2P}$ value represents the spin-spin relaxation time constant of the settled blood cell component of the blood sample. In some embodiments, the settled blood cell component of the blood sample is in the form of a cell pellet. In some embodiments, the $T_{2P}$ value represents the spin-spin relaxation time constant of a blood cell component that is in the form of a pellet of an anti-coagulated whole blood sample.

In some embodiments, the $T_{2P}$ value is represented in the following formula for a $T_2$ relaxation decay curve:

$$I(t) = \sum_i A_i e^{-t/T_{2i}}$$

In some embodiments, I(t) represents the nuclear magnetic resonance (NMR) signal intensity, $A_i$ represents signal amplitude, and $T_{2i}$ represents the transverse relaxation time constant of ith proton microenvironment or mobility domain. In some embodiments, when i=P, the proton microenvironment being measured is the blood cell pellet in an anti-coagulated, sedimented whole blood sample. As red blood cells outnumber white blood cells and platelets by ~1000:1, the dominant contributor to $T_{2P}$ is the water inside of red blood cells. In some embodiments, the value of $T_{2P}$ is influenced by water interactions with hemoglobin, as $T_{2P}$ probes variations in the concentration, oxygenation and oxidation states of hemoglobin. In some embodiments, the $T_{2P}$ term is resolved from other terms using a suitable multi-exponential fitting algorithm, such as an inverse Laplace transformation or matrix pencil method.

$T_{2P}$ values may be measured in various manners. For instance, in some embodiments, $T_{2P}$ values may be measured through the utilization of a magnetic resonance device, a magnetic resonance relaxometry device, a table-top magnetic resonance device, a miniaturized magnetic resonance device, a benchtop magnetic resonance device, a time-domain magnetic resonance device, a magnetic resonance spectroscopy device, a magnetic resonance imaging device, a nuclear magnetic resonance device, or combinations thereof.

Correlating Measured $T_{2P}$ Value to Hypoxemia

The methods and systems of the present disclosure may correlate measured $T_{2P}$ values to hypoxemia in various manners. For instance, in some embodiments, the correlation includes correlating a lower than average $T_{2P}$ value to hypoxemia. In some embodiments, the lower than average $T_{2P}$ value includes a $T_{2P}$ value lower than 270 ms. In some embodiments, the lower than average $T_{2P}$ value includes a $T_{2P}$ value lower than 250 ms. In some embodiments, the lower than average $T_{2P}$ value includes a $T_{2P}$ value lower than 230 ms. In some embodiments, the lower than average $T_{2P}$ value includes a $T_{2P}$ value lower than 200 ms. In some embodiments, the lower than average $T_{2P}$ value includes a $T_{2P}$ value lower than 180 ms. In some embodiments, the lower than average $T_{2P}$ value includes a $T_{2P}$ value lower than 160 ms. In some embodiments, the lower than average $T_{2P}$ value includes a $T_{2P}$ value lower than 140 ms.

In some embodiments, the lower-than-average $T_{2P}$ value is correlated to hypoxemia by referring to results from a human observational or case-control study, where the cases of hypoxemia (e.g., established by blood gas analysis) have $T_{2P}$ values lower than controls without hypoxemia. In some embodiments, the case-control data can be used to calibrate the optimal $T_{2P}$ cutpoint for detecting hypoxemia, as well as the sensitivity, specificity, and positive and negative predictive values.

In some embodiments, the lower-than-average $T_{2P}$ value is correlated to hypoxemia by referring to regression equations that predict hypoxemia or values of its markers (e.g., percent MetHb or percent deoxy-Hb) from a measured $T_{2P}$ value. In some embodiments, the regression equations are established from a study of human subjects with varying degrees of hypoxemia.

In some embodiments, the lower-than-average $T_{2P}$ value is correlated to hypoxemia through multi-variable regression analysis of human research data, leading to equations that mathematically predict hypoxemia or its markers (percent MetHb or percent deoxy-hemoglobin) from measured $T_{2P}$ values. In some embodiments, the regression equations are established using conventional parametric or non-parametric statistical regression analysis. In some embodiments, the regression analysis is performed using machine-learning or artificial intelligence algorithms.

In some embodiments, a lower-than-average $T_{2P}$ value is attributed to decreased oxygenation of hemoglobin. In some embodiments, a lower-than-average $T_{2P}$ value is attributed to increased oxidation of hemoglobin. In some embodiments, the lower-than-average $T_{2P}$ value is attributed to elevated levels of deoxyhemoglobin (deoxy-Hb). In some embodiments, the lower-than-average $T_{2P}$ value is attributed to elevated levels of oxidized hemoglobin (MetHb). In some embodiments, the lower-than-average $T_{2P}$ value is attributed to elevated levels of both MetHb and deoxy-Hb.

Correlating Measured $T_{2P}$ Value to Hypoxemia-Related Conditions

In some embodiments, the methods and systems of the present disclosure also include steps or programming instructions for correlating a measured $T_{2P}$ value to a subject's susceptibility to one or more hypoxemia-related conditions. For instance, in some embodiments, a lower-than-average $T_{2P}$ value is correlated to a subject's susceptibility to one or more hypoxemia-related conditions.

Measured $T_{2P}$ values may be correlated to various hypoxemia-related conditions. For instance, in some embodiments, the hypoxemia-related conditions include, without limitation, hypoxia, cellular damage, tissue damage, type 2 diabetes, cardiovascular disease, hyperinsulinemia, insulin resistance, inflammation, oxidative stress, dyslipidemia, hyperglycemia, early metabolic imbalance, prediabetes, metabolic syndrome, adiposity, or combinations thereof.

Treatment Decisions

In some embodiments, the methods and systems of the present disclosure also include a step or programming instructions for making a treatment decision. In some embodiments, the treatment decision is based on the measured $T_{2P}$ value. In some embodiments, the methods and systems of the present disclosure also include steps or programming instructions for repeating hypoxia detection after implementing the treatment decision. In some embodiments, the methods of the present disclosure also include a step of implementing the treatment decision.

The methods and systems of the present disclosure may make various treatment decisions. For instance, in some embodiments, the treatment decision includes monitoring the subject for signs or symptoms of hypoxemia, administering a therapeutic agent to the subject, or combinations thereof. In some embodiments, the treatment decision includes monitoring the subject for signs or symptoms of hypoxemia. In some embodiments, the treatment decision includes monitoring the subject for signs or symptoms of hypoxemia-related conditions. In some embodiments, the hypoxemia-related conditions include, without limitation, hypoxia, cellular damage, tissue damage, type 2 diabetes, cardiovascular disease, hyperinsulinemia, insulin resistance, inflammation, oxidative stress, dyslipidemia, hyperglycemia, early metabolic imbalance, prediabetes, metabolic syndrome, adiposity, or combinations thereof.

In some embodiments, the treatment decision includes administering a therapeutic agent to the subject. In some embodiments, the treatment decision includes administering an intervention program for the subject. In some embodiments, the intervention program includes, without limitation, a nutritional program, a physical activity program, a non-pharmaceutical intervention, or combinations thereof.

Subjects

The methods and systems of the present disclosure may be utilized to detect hypoxemia in various subjects. For instance, in some embodiments, the subject is a human being. In some embodiments, the subject is a healthy subject. In some embodiments, the subject is not suffering from or diagnosed with hypoxemia. In some embodiments, the subject shows no hypoxemia-related symptoms.

In some embodiments, the subject suffers from hypoxemia. In some embodiments, the hypoxemia includes subclinical hypoxemia. In some embodiments, the hypoxemia includes clinical hypoxemia.

Operation Methods

The methods of the present disclosure can occur in various manners. For instance, in some embodiments, the methods of the present disclosure occur manually.

In some embodiments, the methods of the present disclosure occur through the utilization of a computer program. In some embodiments, the computer program includes a web-based program, an application-based program, or combinations thereof. In some embodiments, the computer program implements a multi-exponential analysis to extract the $T_{2P}$ value from the raw multi-exponential decay curve. In some embodiments, the computer program implements an inverse Laplace transform algorithm or a matrix pencil algorithm for multi-exponential analysis.

In some embodiments, the computer program includes a machine-learning or artificial intelligence algorithm. In some embodiments, the machine learning or artificial intelligence algorithm is trained on the $T_{2P}$ values and correlated measurements (e.g., correlated health markers). In some embodiments, the training of the machine learning algorithm is conducted using a random forest or bootstrap forest procedure to assess the correlation between $T_{2P}$ and health markers.

In some embodiments, the machine learning or artificial intelligence algorithm is an L1-regularized logistic regression algorithm. In some embodiments, the machine learning or artificial intelligence algorithm includes supervised learning algorithms. In some embodiments, the supervised learning algorithms include nearest neighbor algorithms, naïve-Bayes algorithms, decision tree algorithms, linear regression algorithms, support vector machines, neural networks, convolutional neural networks, ensembles (e.g., random forests and gradient-boosted decision trees), or combinations thereof.

Systems

The systems of the present disclosure may have various architectures and forms. For instance, in some embodiments, the systems of the present disclosure are in the form of a web-based program, an application-based program, or combinations thereof. In some embodiments, the systems of the present disclosure include a machine-learning algorithm or artificial intelligence algorithm. In some embodiments, the machine learning algorithm or artificial intelligence algorithm is trained on the $T_{2P}$ values and correlated measurements (e.g., correlated health markers).

The systems of the present disclosure can include various types of computer-readable storage mediums. For instance, in some embodiments, the computer-readable storage medium can be a tangible device that can retain and store instructions for use by an instruction execution device. In some embodiments, the computer-readable storage medium may include, without limitation, an electronic storage device, a magnetic storage device, an optical storage device, an electromagnetic storage device, a semiconductor storage device, or combinations thereof. A non-exhaustive list of more specific examples of suitable computer-readable storage medium includes, without limitation, a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device, or combinations thereof.

A computer-readable storage medium, as used herein, is not to be construed as being transitory signals per se. Such transitory signals may be represented by radio waves or other freely propagating electromagnetic waves, electromagnetic waves propagating through a waveguide or other transmission media (e.g., light pulses passing through a fiber-optic cable), or electrical signals transmitted through a wire.

In some embodiments, computer-readable program instructions for systems can be downloaded to respective computing/processing devices from a computer-readable storage medium or to an external computer or external storage device via a network, such as the Internet, a local area network (LAN), a wide area network (WAN) and/or a wireless network. In some embodiments, the network may include copper transmission cables, optical transmission fibers, wireless transmission, routers, firewalls, switches, gateway computers and/or edge servers. In some embodiments, a network adapter card or network interface in each computing/processing device receives computer-readable program instructions from the network and forwards the computer-readable program instructions for storage in a computer-readable storage medium within the respective computing/processing device.

In some embodiments, computer-readable program instructions for carrying out operations of the present disclosure may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object-oriented programming language such as Smalltalk, C++, or the like, and procedural programming languages, such as the "C" programming language or similar programming languages.

In some embodiments, the computer-readable program instructions may execute entirely on the user's computer, partly on the user's computer, as a stand-alone software package, partly on the user's computer and partly on a remote computer or entirely on the remote computer or server. In the latter scenario, the remote computer may be connected in some embodiments to the user's computer through any type of network, including a LAN or a WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry in order to perform aspects of the present disclosure.

Figure 1B:
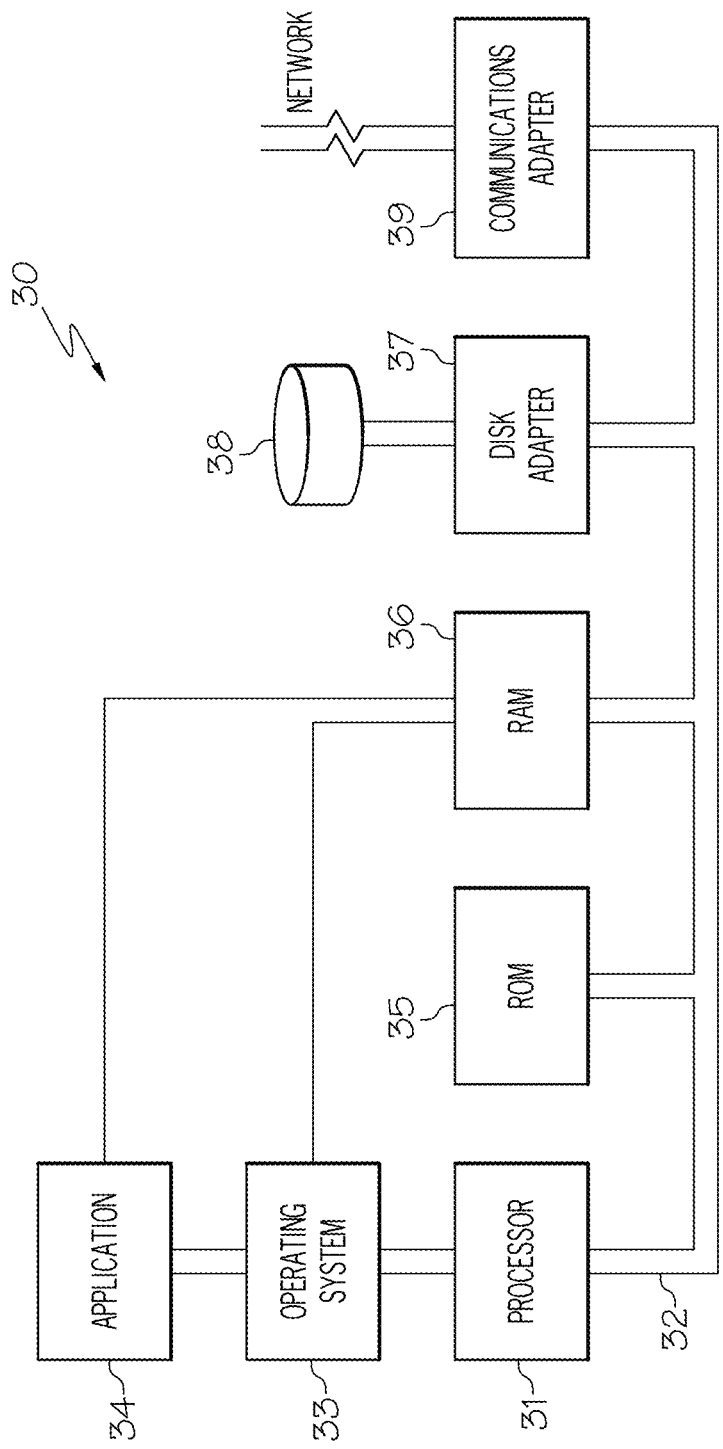
FIG. 1B illustrates a system for detecting hypoxemia in a subject.

Embodiments of the present disclosure for detecting hypoxemia as discussed herein may be implemented using a system illustrated in FIG. 1B. Referring now to FIG. 1B, FIG. 1B illustrates an embodiment of the present disclosure of the hardware configuration of a system 30 which is representative of a hardware environment for practicing various embodiments of the present disclosure.

System 30 has a processor 31 connected to various other components by system bus 32. An operating system 33 runs on processor 31 and provides control and coordinates the functions of the various components of FIG. 1B. An application 34 in accordance with the principles of the present disclosure runs in conjunction with operating system 33 and provides calls to operating system 33, where the calls implement the various functions or services to be performed by application 34. Application 34 may include, for example, a program for detecting hypoxemia as discussed in the present disclosure, such as in connection with FIGS. 1A, 2A-2B, and 3-12.

Referring again to FIG. 1B, read-only memory ("ROM") 35 is connected to system bus 32 and includes a basic input/output system ("BIOS") that controls certain basic functions of system 30. Random access memory ("RAM") 36 and disk adapter 37 are also connected to system bus 32. It should be noted that software components including operating system 33 and application 34 may be loaded into RAM 36, which may be system's 30 main memory for execution. Disk adapter 37 may be an integrated drive electronics ("IDE") adapter that communicates with a disk unit 38 (e.g., a disk drive). It is noted that the program for detecting hypoxemia, as discussed in the present disclosure, such as in connection with FIGS. 1A, 2A-2B, and 3-12 may reside in disk unit 38 or in application 34.

System 30 may further include a communications adapter 39 connected to system bus 32. Communications adapter 39 interconnects system bus 32 with an outside network (e.g., wide area network) to communicate with other devices.

Aspects of the present invention are described herein with reference to flowchart illustrations and/or block diagrams of methods, apparatus (systems), and systems according to embodiments of the invention. It will be understood that each block of the flowchart illustrations and/or block diagrams and combinations of blocks in the flowchart illustrations and/or block diagrams can be implemented by computer-readable program instructions.

These computer-readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein includes an article of manufacture including instructions which implement aspects of the function/act specified in the flowchart and/or block diagram block or blocks. The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and systems according to various embodiments of the present disclosure. In this regard, each block in the flowchart or block diagrams may represent a module, segment, or portion of instructions, which includes one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Magnetic Resonance Devices

Additional embodiments of the present disclosure pertain to magnetic resonance devices. In some embodiments, the magnetic resonance device is optimized for measuring whole blood $T_{2P}$ values (e.g., in a sample obtained by fingerstick, armstick or venipuncture). In some embodiments, the magnetic resonance device is operable to detect hypoxemia in a subject in accordance with the methods of the present disclosure.

In some embodiments, the magnetic resonance device includes, without limitation, a magnetic resonance relaxometry device, a table-top magnetic resonance device, a miniaturized magnetic resonance device, a benchtop magnetic resonance device, a time-domain magnetic resonance device, a magnetic resonance spectroscopy device, a magnetic resonance imaging device, a nuclear magnetic resonance device, or combinations thereof. In some embodiments, the magnetic resonance device is in the form of an instrument. In some embodiments, the magnetic resonance device is in the form of a nuclear magnetic resonance device. In some embodiments, the magnetic resonance device is in the form of a table-top miniaturized or portable magnetic resonance device.

In some embodiments, the magnet air gap and probe are reduced in diameter and optimized for small sample tubes containing human blood. In some embodiments, a cylindrical sample tube or capillary tube 3 mm or less in diameter is used. This tube geometry permits the use of magnet air gaps much smaller than typically used in commercially available magnetic resonance devices. In some embodiments, the magnet air gap and probe are optimized for non-cylindrical sample tubes, chambers or holders.

Figure 13A:
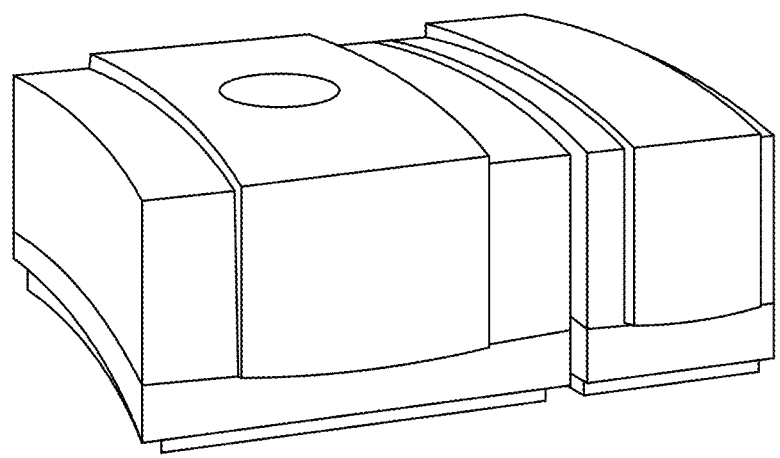
FIGS. 13A-13C show non-limiting examples of benchtop, portable or miniaturized nuclear magnetic resonance (NMR) relaxometry devices that can measure $T_{2P}$.
Figure 13B:
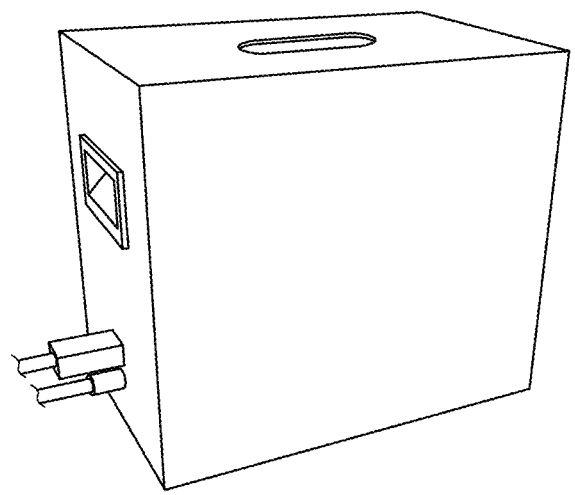
Figure 13C:
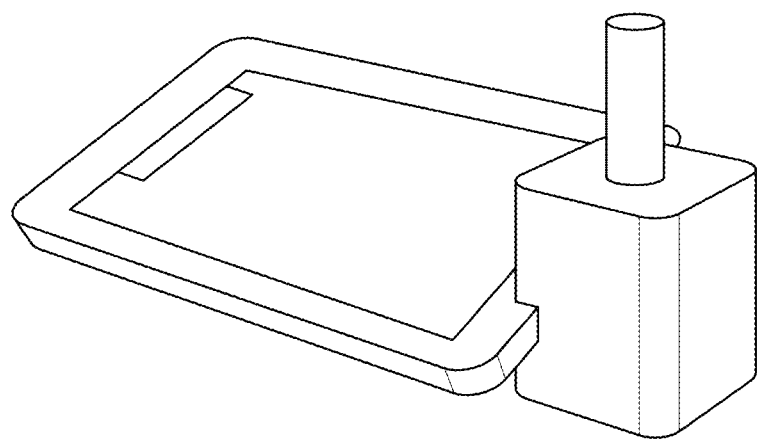

In some embodiments, the device includes a low-field permanent magnet. In some embodiments, the magnet field strength is 0.47 Tesla, corresponding to approximately 20 MHz for $^1H$. In some embodiments, the magnetic field strength is approximately 0.235 Tesla, corresponding to approximately 10 MHz for $^1H$. In some embodiments, the magnet field strength is approximately 1 Tesla, corresponding to approximately 42.6 MHz for $^1H$. FIGS. 13A-13C illustrate additional exemplary devices.

Additional Embodiments

Reference will now be made to more specific embodiments of the present disclosure and experimental results that provide support for such embodiments. However, Applicant notes that the disclosure below is for illustrative purposes only and is not intended to limit the scope of the claimed subject matter in any way.

Example 1. Whole Blood Tar Links Hemoglobin Status to Metabolic Health

Plasma and serum water $T_2$, measured using benchtop magnetic resonance relaxometry, are global biomarkers of cardiometabolic health and metabolic syndrome. This Example investigated whether $T_2$ measured using whole blood yields similar information, as fingerstick or armstick whole blood samples would simplify metabolic health screening in point-of-care settings.

Anti-coagulated blood samples from 44 asymptomatic, non-diabetic subjects were analyzed immediately after venipuncture using a 0.47T benchtop relaxometer operating at 20 MHz for $^1H$. Whole blood water $T_2$ values, measured using a Carr-Purcell-Meiboom-Gill pulse sequence and analyzed using discrete inverse Laplace transformation, were compared with over 100 health measures using bivariate correlation and multi-variable linear regression analyses, as well as predictor screening using a random forests or bootstrap forests machine learning algorithm.

Spontaneously-settled whole blood yielded two well-resolved components assigned to the plasma supernatant ($T_{2S}$) and cell pellet ($T_{2P}$). Paradoxically, $T_{2S}$ correlated with hematocrit and red cell count, even though the supernatant contained no blood cells. Upon mixing whole blood with its own plasma, an inverse sixth-power dependence of $T_{2S}$ on hematocrit was observed. This dependence was attributed to the paramagnetic relaxation enhancement of supernatant water resulting from a magnetic susceptibility difference with the paramagnetic pellet. Using this sixth-power dependence, plasma water $T_2$ can be estimated by extrapolation. Whole blood $T_{2P}$ probes the state of hemoglobin inside red blood cells. Surprisingly, $T_{2P}$ revealed correlations with markers of hyperinsulinemia, insulin resistance, oxidative stress, inflammation, adiposity, dyslipidemia, hypoxia, and cellular damage.

Water $T_{2S}$ and $T_{2P}$ measured in settled whole blood can detect metabolic dysregulation, early metabolic imbalance or metabolic syndrome in generally healthy subjects. The results for $T_{2P}$ identify a novel linkage between hemoglobin oxygenation status and metabolic health. This discovery establishes the feasibility of personalized health screening using whole blood magnetic resonance relaxometry.

Example 1.1. Human Subject Recruitment Protocol

Applicant conducted an observational cross-sectional study on 44 asymptomatic, non-diabetic human subjects who were recruited through an Institutional Review Board (IRB) protocol approved by the Institutional Review Board of the University of North Texas Health Science Center Fort Worth. The inclusion criteria were adults aged 18 and up, weighing at least 110 pounds. The exclusion criteria were diabetes (history or fasting glucose≥125 mg/dL or A1c≥6.5), other active acute or chronic disease (history or CRP≥10), history of bleeding disorders or difficulty donating blood, confirmed or suspected pregnancy, or not fasting at least 12 hours. All subjects were required to abstain from alcohol, exercise, over-the-counter medications, and nutritional supplements for 24 hours prior to the blood draw. The blood samples were drawn by a registered nurse-phlebotomist in the morning after an overnight fast.

Example 1.2. NMR and Biomarker Measurements

Within 1 hour of blood collection, whole blood $T_2$ profiles were acquired on a Bruker mq20 Minispec (0.47T, 20 MHz for 41) using a modified Carr-Purcell-Meiboom-Gill (CPMG) pulse sequence. The sample configuration and pulse sequence are described elsewhere (*J Transl Med.* 2017; 15(1):258. doi: 10.1186/s12967-017-1359-5.) For settled blood NMR measurements, the sample was allowed to spontaneously sediment in the 3 mm co-axial NMR insert for 40 min, and for the mixed blood, the samples were gently vortexed immediately prior to CPMG acquisition. The decay curve was analyzed with a discrete inverse Laplace algorithm (XPFit, Alango Ltd.) to extract water $T_2$ values.

Immediately after the phlebotomy, blood samples were processed to isolate serum and plasma for biomarker measurements. On the same day, whole blood, plasma or serum samples were sent to a CLIA-approved clinical laboratory (Atherotech or Quest) for diagnostic testing and biomarker analysis as described (*J Transl Med.* 2017; 15(1):258. doi: 10.1186/s12967-017-1359-5.) Briefly, biomarkers of insulin and glucose metabolism, lipid and lipoprotein metabolism, inflammation, blood cells, liver, kidney and thyroid function were obtained. Whole blood and plasma viscosity were measured in-house using a VISCOLAB3000. The insulin resistance indices HOMA (homeostasis model assessment) and McAuley were calculated using the formula described in *Diabetologia.* 1985; 28(7):412-419, and *Diabetes Care.* 2001; 24(3):460-464, respectively.

Example 1.3. Cell Supernatant Height and NMR Relaxation

Briefly, blood samples with different hematocrit levels were artificially generated by either adding plasma (diluting the blood cells) or removing plasma (concentrating the blood cells) from the blood samples after a brief centrifugation. Blood samples with a hematocrit as low as ~20% and as high as ~95% were generated by this method. The blood samples with artificially generated hematocrit were allowed to sediment before CPMG data collection, as described in the protocol for settled blood NMR relaxometry.

Example 1.4. Data Analysis

The number of subjects (N=44) yielded a statistical power of 0.8 at a correlation coefficient of 0.4 and alpha=0.05. The decay curve acquired from each blood sample was analyzed to extract $T_2$ values using XPFit version 1.2.1, Alango Ltd. The decay curve for settled blood gave rise to two resolved $T_2$ time constants, each corresponding to supernatant and cell pellet $T_2$. Applicant designated these $T_2$ time constants as $T_{2S}$ and $T_{2P}$, respectively. All other statistical analyses were performed using JMP®, Version 12.1.0 (SAS Institute Inc., Cary, NC), GraphPad Prism v. 6.05 (GraphPad Software, Inc.) and R 3.1.4 using package stats and ggplot2. The biomarker data, including in-house measurements, were log-transformed if positively skewed. Pearson's bivariate correlations were obtained between blood water $T_2$ and other biomarkers. Due to occasional clinical laboratory errors in the processing of samples or sample degradation during transport, the N for a given correlation may have differed slightly.

For t-test, logistic regression and receiver operator characteristic (ROC) curve analyses, the cohort was divided into two groups of individuals having McAuley index >6.07 (No IR) and ≤6.07 (IR). Similarly, two groups of IR and No IR were defined based on the tertile criteria of six insulin resistance/glucose tolerance biomarkers (insulin, insulin c-peptide, McAuley index, triglyceride, glucose and $Hb_{A1c}$). In this method, the subjects were classified as insulin resistant if two or more of these six biomarkers fell in the top tertile. Student's t-test was then performed for whole blood $T_{2P}$ in order to check whether the mean of $T_{2P}$ was significantly different between these two groups. Finally, receiver operator characteristic (ROC) curve analyses were analyzed to compare the sensitivity and specificity of settled blood $T_{2P}$ for detecting hyperinsulinemia/insulin resistance.

Example 1.5. Characteristics of Human Subjects

Table 1 shows the clinical characteristics of the human subjects recruited in this Example. Overall, this is a cohort of asymptomatic adults spanning a wide age range. Although some biomarker values for specific individuals were outside the normal reference ranges, the mean values for the cohort were within those ranges. Based on $Hb_{A1c}$ and fasting glucose values, 15 subjects had prediabetes and 29 were normoglycemic. None of the 44 subjects met the criteria for overt diabetes.

TABLE 1

Characteristics of the human study population (N = 44).

| Parameter | Mean ± SD | Range | Reference Values[1] |
|---|---|---|---|
| Age | 36 ± 13 | 23-61 | n/a |
| Gender | n/a | 20 female, 24 male | n/a |
| Weight (kg) | 76.1 ± 19.3 | 51.7-152.0 | n/a |
| BMI (kg/m$^2$) | 26.2 ± 5.2 | 19.1-45.1 | >25 (kg/m$^2$) |
| Settled blood $T_{2P}$ (ms) | 248.7 ± 20 | 191.7-293.0 | n.d. |
| Settled blood $T_{2S}$ (ms) | 719.2 ± 61.7 | 578.2-857.1 | n.d. |
| Mixed blood $T_2$ (ms) | 299.7 ± 34 | 224.7-384.8 | n.d. |
| Glucose, fasting (mg/dL) | 90.6 ± 7.6 | 71.0-109.0 | <100, non-diabetes<br>100-125, prediabetes<br>>125, diabetes |
| HbA$_{1c}$ (%) | 5.5 ± 0.3 | 4.7-6.1 | <5.7, non-diabetes<br>5.7-6.4, prediabetes<br>≥6.5, diabetes |
| Insulin, fasting (μIU/mL) | 8.3 ± 6.5 | 2.2-40.1 | <12.2 |
| Insulin C-peptide, fasting (ng/mL) | 1.7 ± 0.8 | 0.7-5.1 | <2.85 |
| Triglycerides, fasting (mg/dL) | 116.7 ± 54.1 | 50.0-276.0 | <150 |
| hs-CRP (mg/L) | 2.4 ± 2.7 | 0.05-9.6 | <1.0, low CVD risk<br>1.0-3.0, average risk<br>>3.0, high risk<br>≥10, active illness |
| WBC count (×10$^3$/mL) | 6.6 ± 1.6 | 3.9-11.2 | 3.4-10.8 |
| Neutrophil count (×10$^3$/mL) | 3.5 ± 1.1 | 1.8-7.2 | 1.4-7.0 |
| RBC count (×10$^6$/mL) | 4.7 ± 0.5 | 3.8-5.8 | 4.7-6.1 (male)<br>4.2-5.4 (female) |
| Total cholesterol (mg/dL) | 181.6 ± 41.2 | 97.0-276.0 | <200 |
| HDL-C (mg/dL) | 52.1 ± 12.7 | 31.0-78.0 | ≥40 male, ≥50 female |
| LDL-C (mg/dL) | 107.3 ± 33.2 | 50.0-180.0 | <130 |
| Total serum protein (g/dL) | 7.1 ± 0.3 | 6.3-8.0 | 6.1-8.1[2] |
| Serum viscosity (cP) | 1.2 ± 0.1 | 0.9-1.4 | 1.3 ± 0.06[2] |
| Plasma viscosity (cP) | 1.4 ± 0.2 | 1.2-2.0 | 1.4 ± 0.08[2] |
| Blood viscosity (cP) | 3.1 ± 0.4 | 2.2-4.2 | 3.26 ± 0.43[2]<br>(at shear-rate of 100 s$^{-1}$) |
| Thyroid stimulating hormone (mIU/mL) | 2.7 ± 1.9 | 0.01-8.31 | 0.5-4.5 |

[1]All reference values are from Quest or Labcorp, unless noted otherwise;
[2]viscosity reference;
n.d., not determined;
n/a, not applicable.

Example 1.6. Spontaneous Sedimentation and Blood Water $T_2$

Figure 2A:
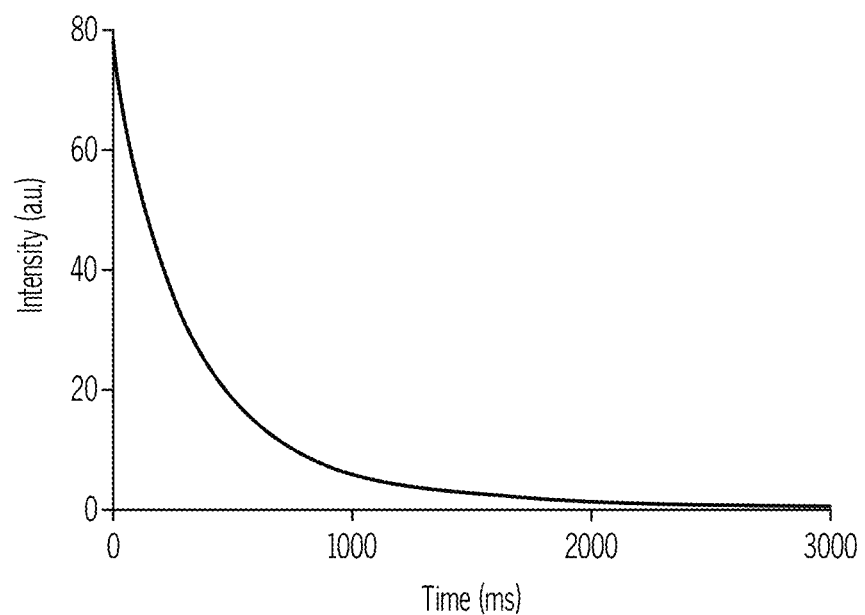
FIGS. 2A-2B show samples of a Carr-Purcell-Meiboom-Gill (CPMG) decay curve and a $T_2$ profile.
Figure 2B:
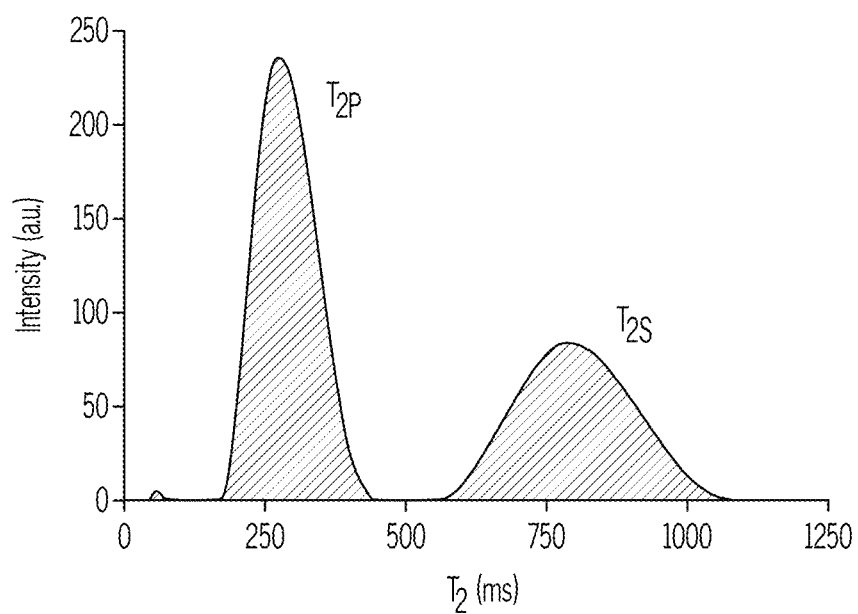
Figure 3:
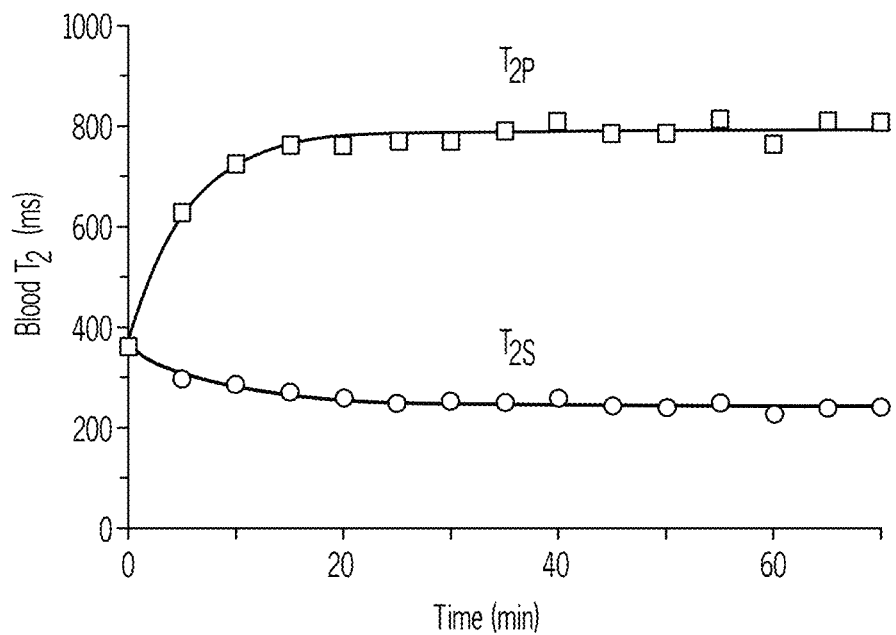
FIG. 3 shows blood sample $T_{2P}$ ($T_2$ relaxation time constant of the blood cells of the blood sample) and $T_{2S}$ ($T_2$ relaxation time constant of the plasma of the blood sample) levels as a function of time. After gentle mixing, a whole blood sample was allowed to sediment spontaneously while collecting a CPMG decay curve every five minutes. The decay curve was analyzed by inverse Laplace transformation. The $T_2$ data are plotted against settling time. After approximately 40 minutes of spontaneous sedimentation, both $T_2$ values reached equilibrium.
Figure 4:
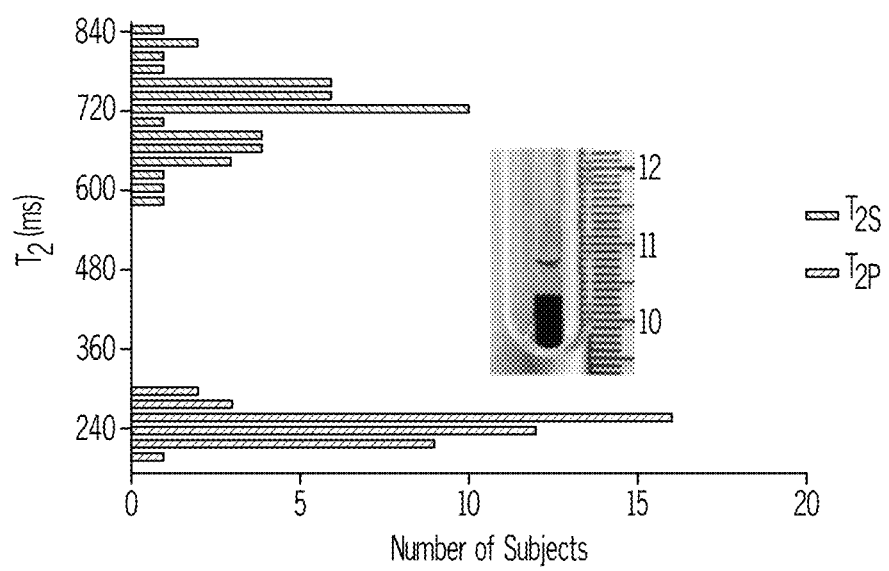
FIG. 4 shows the frequency distribution and variation of $T_2$ values observed for 44 apparently healthy human subjects (bars). The mean±S.D. for $T_{2P}$ was 248.1±20.2 msec, and $T_{2S}$ was 718.6±60.4 msec.

The anti-coagulated blood settled quickly and spontaneously in the NMR tube creating two separate phases. These two phases gave rise to two distinct $T_2$ values, $T_{2S}$ for supernatant and $T_{2P}$ for pellet, as shown in FIGS. 2A-2B. FIG. 3 shows the time-series NMR relaxation results for blood while spontaneously settling. Applicant concluded that at 40 min into sedimentation, the $T_2$ values for both phases had achieved equilibrium. Therefore, Applicant allowed each blood sample to settle 40 min before collecting NMR relaxation data. FIG. 4 shows the histogram of the settled blood $T_2$ values for the human subjects in the study cohort. The correlation between $T_{2P}$ and $T_{2S}$ was low (0.22) with a non-significant p-value (0.15), indicating that the values were likely uncorrelated.

Example 1.7. Correlations of Blood $T_2$ Values with Other Biomarkers

Table 2 lists statistically significant correlations for pellet $T_{2P}$. These correlations include markers of hyperinsulinemia/insulin resistance, glucose tolerance, inflammation and dyslipidemia. Among the strongest correlations, of both negative and positive sign, were HOMA-IR, insulin C-peptide and the McAuley Index: markers of hyperinsulinemia and insulin resistance. Also, a strong correlation was observed with lactate, a marker of hypoxia. Paradoxically, the pattern of correlations was very similar to that observed for plasma water $T_2$, even though the blood cell pellet contains very little plasma and is dominated by packed blood cells.

TABLE 2

Bivariate correlation coefficients for $T_{2P}$ with health measures.

| Health Measure[a] | Huber M (95% CI) | P value | N |
|---|---|---|---|
| Insulin C-peptide* | −0.67 (−0.46, −0.81) | <0.0001 | 43 |
| HOMA2-IR (C-peptide)* | −0.67 (−0.46, −0.81) | <0.0001 | 43 |
| Complement C3c | −0.64 (−0.41, −0.80) | <0.0001 | 40 |
| McAuley Index | +0.62 (+0.39, +0.77) | <0.0001 | 43 |
| Apolipoprotein B | −0.60 (−0.36, −0.76) | <0.0001 | 43 |
| LDL particle number | −0.60 (−0.37, −0.76) | <0.0001 | 43 |
| Non-HDL-cholesterol* | −0.59 (−0.35, −0.75) | <0.0001 | 43 |
| Alanine aminotransferase* | −0.58 (−0.33, −0.75) | <0.0001 | 42 |
| Lactate | −0.57 (−0.32, −0.75) | <0.0001 | 41 |
| Serum water $T_2$ | +0.55 (+0.30, +0.73) | <0.001 | 43 |
| IDL-cholesterol* | −0.55 (−0.27, −0.74) | <0.001 | 36 |
| TG/HDL ratio* | −0.54 (−0.29, −0.72) | <0.001 | 43 |
| Immunoglobulin G | −0.53 (−0.28, −0.72) | <0.001 | 43 |
| Body mass index* | −0.53 (−0.28, −0.72) | <0.001 | 43 |
| LDL-cholesterol | −0.53 (−0.27, −0.71) | <0.001 | 43 |
| Remnant-cholesterol* | −0.51 (−0.22, −0.72) | <0.001 | 36 |
| Insulin* | −0.50 (−0.23, −0.70) | <0.001 | 43 |
| Fibrinogen* | −0.49 (−0.23, −0.69) | <0.001 | 43 |
| Triglycerides* | −0.48 (−0.21, −0.68) | <0.01 | 43 |
| Serum globulins | −0.48 (−0.20, −0.68) | <0.01 | 42 |
| Plasma globulins | −0.48 (−0.20, −0.68) | <0.01 | 41 |

TABLE 2-continued

Bivariate correlation coefficients for $T_{2P}$ with health measures.

| Health Measure[a] | Huber M (95% CI) | P value | N |
|---|---|---|---|
| Total cholesterol | −0.47 (−0.20, −0.68) | <0.01 | 43 |
| Plasma water $T_2$ | +0.45 (+0.17, +0.66) | <0.01 | 42 |
| HOMA2-IR (insulin)* | −0.45 (−0.16, −0.67) | <0.01 | 39 |
| Gamma glutamyl transpeptidase* | −0.44 (−0.16, −0.65) | <0.01 | 43 |
| Lipoprotein-assoc. phospholipase $A_2$ | +0.43 (+0.15, +0.65) | <0.01 | 43 |
| Serum % globulins | −0.41 (−0.12, −0.64) | <0.01 | 42 |
| Complement C4c* | −0.40 (−0.11, −0.64) | <0.01 | 40 |
| Age* | −0.40 (−0.11, −0.62) | <0.01 | 43 |
| VLDL-cholesterol* | −0.40 (−0.08, −0.64) | <0.05 | 36 |
| Plasminogen activator inhibitor-1* | −0.39 (−0.10, −0.62) | <0.05 | 43 |
| Total plasma protein | −0.38 (−0.09, −0.62) | <0.05 | 41 |
| HDL-cholesterol | +0.38 (+0.09, +0.61) | <0.05 | 43 |
| Body temperature | −0.37 (−0.08, −0.60) | <0.05 | 43 |
| Plasma % globulins | −0.36 (−0.06, −0.60) | <0.05 | 41 |
| Erythrocyte sedimentation rate | −0.35 (−0.05, −0.60) | <0.05 | 41 |
| C-reactive protein (hs-CRP) | −0.31 (−0.01, −0.56) | <0.05 | 43 |

*these variables were natural log transformed for analysis;
†HOMA-IR (GC) is calculated from glucose and insulin C-peptide, while HOMA-IR (GI) is calculated from glucose and insulin as described in (*Diabetologia.* 1985; 28(7): 412-419).

Table 3 lists statistically significant correlations for supernatant $T_{2S}$. While some correlations expected for plasma were observed, the strongest correlations were with hematocrit and red blood cell count. That result was not anticipated.

TABLE 3

Statistically significant Pearson's product moment correlations of settled blood $T_{2S}$ with blood biomarkers.

| Biomarker | Pearson's correlation | P-value | N |
|---|---|---|---|
| Hematocrit | −0.608 | <0.001 | 45 |
| Red blood cell count | −0.593 | <0.001 | 45 |
| Blood viscosity 37 C. | −0.550 | <0.001 | 44 |
| Plasma total protein | −0.547 | <0.001 | 43 |
| Hemoglobin | −0.536 | <0.001 | 45 |
| IDL | −0.491 | 0.002 | 36 |
| Remnant lipoprotein | −0.485 | 0.003 | 36 |
| Plasma viscosity 37 C. | −0.482 | 0.001 | 45 |
| Total Protein | −0.474 | 0.001 | 44 |
| Albumin | −0.468 | 0.001 | 44 |
| Total LDL | −0.453 | 0.002 | 45 |
| Non HDL cholesterol | −0.443 | 0.002 | 45 |
| ApoB | −0.442 | 0.002 | 45 |
| ApoB to ApoA1 ratio | −0.436 | 0.008 | 36 |
| Total Cholesterol | −0.414 | 0.005 | 45 |
| Total VLDL | −0.392 | 0.018 | 36 |
| LDL-P | −0.383 | 0.009 | 45 |
| Triglycerides | −0.353 | 0.018 | 45 |
| HOMA IR (GC) | −0.343 | 0.021 | 45 |
| Serum viscosity 37 C. | −0.336 | 0.024 | 45 |
| Insulin c-peptide | −0.331 | 0.026 | 45 |
| Plasma albumin | −0.329 | 0.031 | 43 |
| Plasma globulin | −0.327 | 0.032 | 43 |
| Glucose | −0.309 | 0.039 | 45 |
| Fibronectin | −0.303 | 0.043 | 45 |
| Homocysteine | −0.298 | 0.047 | 45 |
| Body temperature C. | 0.304 | 0.042 | 45 |
| MCHC | 0.317 | 0.034 | 45 |
| McAuley Index | 0.362 | 0.015 | 45 |
| Chloride | 0.389 | 0.009 | 44 |
| Plasma $T_2$ | 0.517 | <0.001 | 44 |
| Serum $T_2$ | 0.557 | <0.001 | 45 |

Mixed blood, as shown in Table 4, revealed only a few significant correlations, which are predominantly hemoglobin and related markers. To further investigate the unexpected association of $T_{2S}$ with hematocrit, Applicant artificially expanded the range of hematocrit values normally observed in human blood by mixing blood cells with their own plasma, either diluting or concentrating the blood cell fraction. This permitted Applicant to examine the dependence of $T_{2S}$ over a wider range of hematocrit values. The results are shown in FIG. 6. A steep dependence is seen at high hematocrit values, where the average distance between water in the supernatant and the pellet interface is small. The points fit well to an equation with a sixth power dependence on hematocrit. The sixth power dependence pointed to paramagnetic relaxation enhancement as the likely cause.

TABLE 4

Statistically significant Pearson's product moment correlations of mixed blood $T_2$ with blood biomarkers.

| Biomarker | Pearson's correlation | P-value | N |
|---|---|---|---|
| Hemoglobin | −0.812 | <0.001 | 35 |
| Hematocrit | −0.801 | <0.001 | 35 |
| Red blood cell count | −0.634 | <0.001 | 35 |
| Blood viscosity 37 C. | −0.566 | <0.001 | 34 |
| Albumin | −0.463 | 0.006 | 34 |
| ApoB toApo-A1 ratio | −0.434 | 0.024 | 27 |
| Albumin to globulin ratio | −0.376 | 0.028 | 34 |
| Homocysteine | −0.363 | 0.032 | 35 |
| Ceruloplasmin | 0.347 | 0.041 | 35 |
| Platelet count | 0.384 | 0.023 | 35 |
| Cortisol | 0.412 | 0.014 | 35 |
| ESR | 0.435 | 0.011 | 33 |
| Alpha-1 antitrypsin | 0.589 | <0.0010 | 35 |

Figure 7:
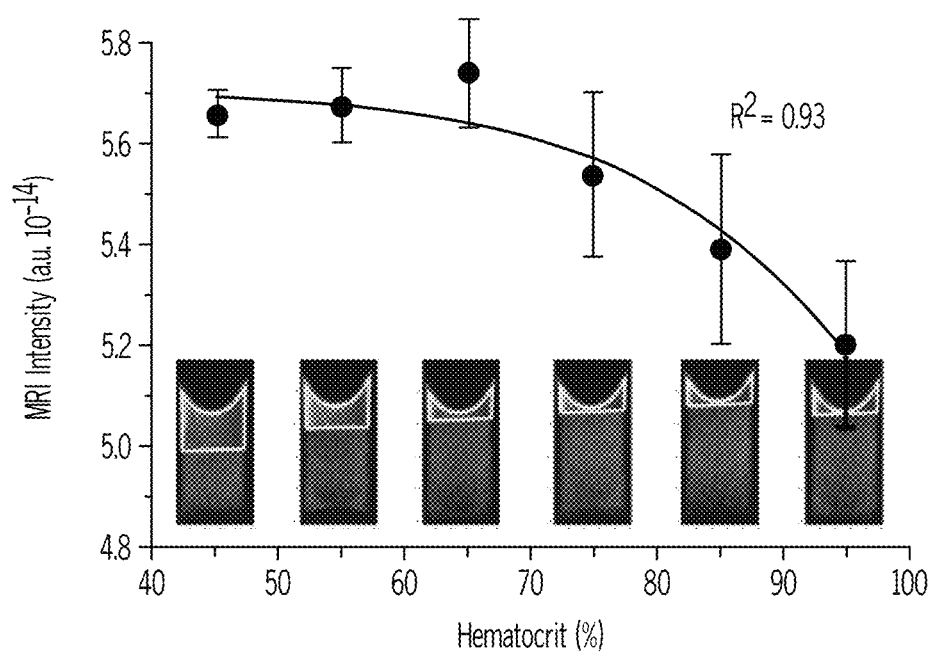
FIG. 7 shows the dependence of signal intensity from $T_2$-weighted images on hematocrit, derived from benchtop MRI analysis of settled whole blood.

To further assess the paramagnetic relaxation enhancement (PRE) effect, Applicant collected $T_2$-weighted images using a benchtop MRI instrument and analyzed the signal intensities of slices through the supernatant. As shown in FIG. 7, the intensities also revealed a sixth-power dependence on hematocrit, although the precision of the MRI intensity measurements was not nearly as good as the precision of the quantitative $T_2$ measurements from benchtop relaxometry.

Figure 8:
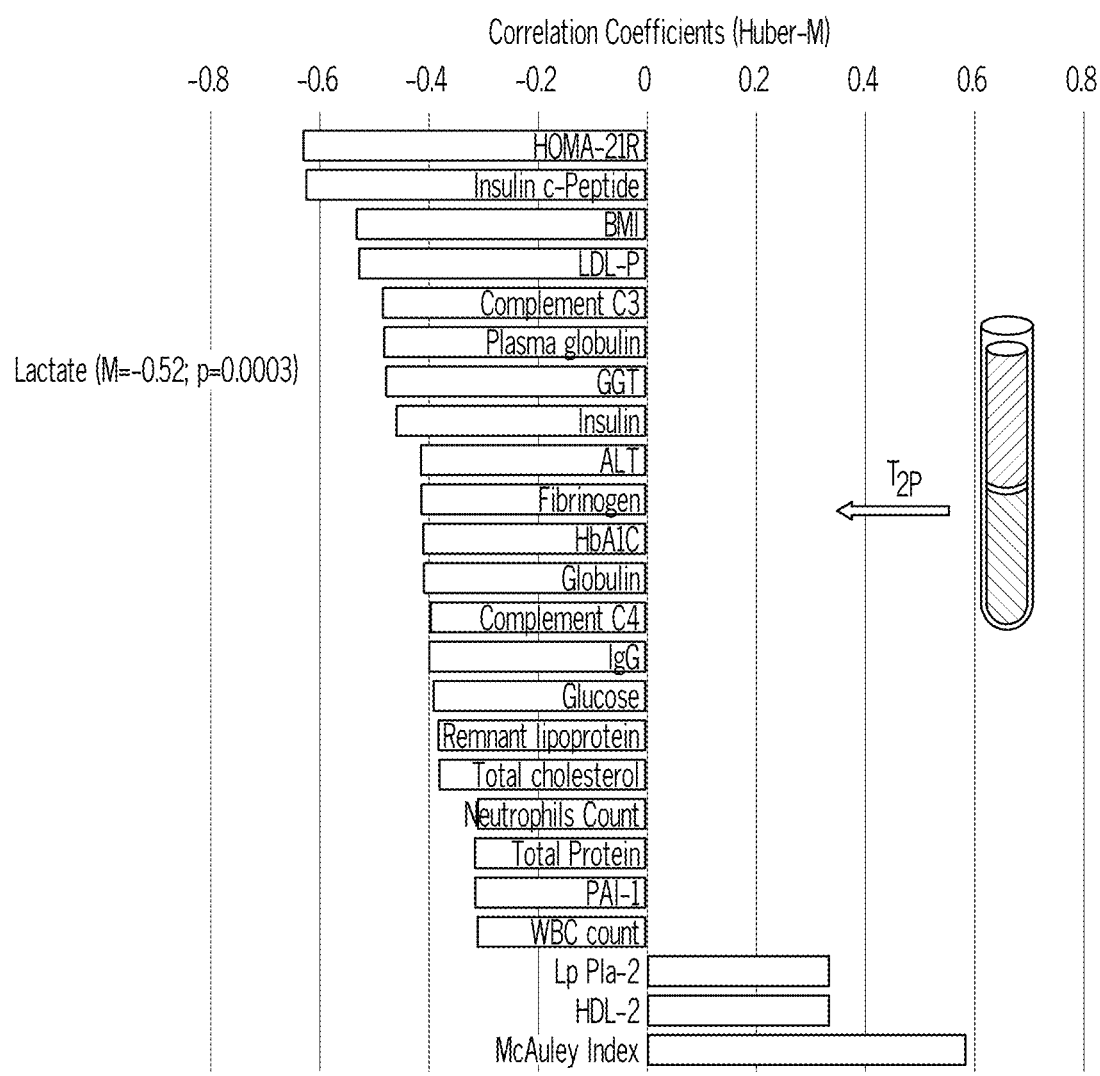
FIG. 8 shows correlation coefficients (Huber M-values) for $T_{2P}$ and biomarkers of cardiometabolic health.

FIG. 8 provides a summary of correlation coefficients (Huber M-values) for $T_{2P}$ and biomarkers of cardiometabolic health. These observations were unexpected, as $T_{2P}$ monitors hemoglobin status. Confidence intervals and p-values are not shown. However, all of the correlation coefficients in FIG. 8 were statistically significant (p<0.05).

FIG. 9 provides a hypothetical mechanistic link whereby hemoglobin oxidation (subclinical met-hemoglobinemia) mediates the association between hyperinsulinemia and downstream hypoxia and chronic inflammation. FIG. 10 illustrates a causal mediation analysis to test the hypothesis in FIG. 9, using four (4) linked regression equations. The variables highlighted in red were statistically significant in the linked equations. The observed p-values for lactate as the outcome variable, insulin as the exposure and $T_{2P}$ as the mediator, are listed.

Figure 11:
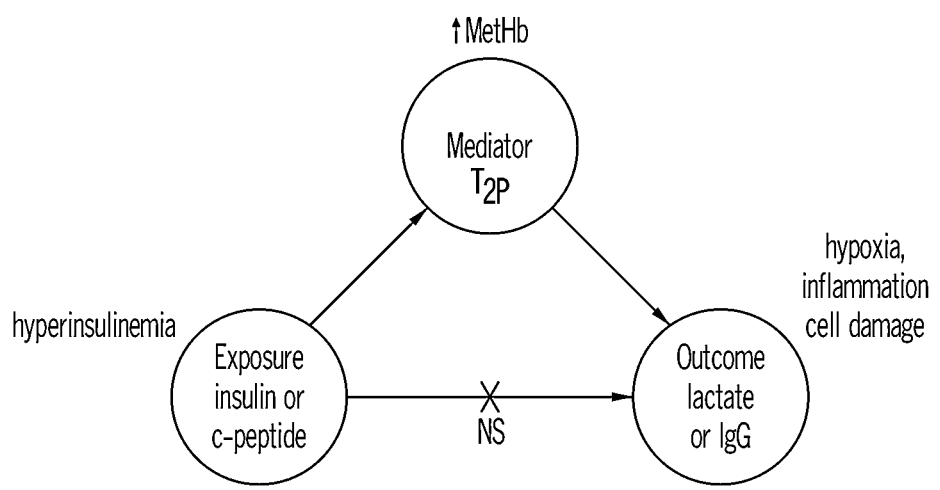
FIG. 11 shows a schematized representation of the results reported in FIG. 10.

FIG. 11 provides a schematized representation of the results reported in FIG. 10. When the regression equation includes the mediator ($T_{2P}$), the association between exposure and outcome is non-significant (NS).

Figure 12:
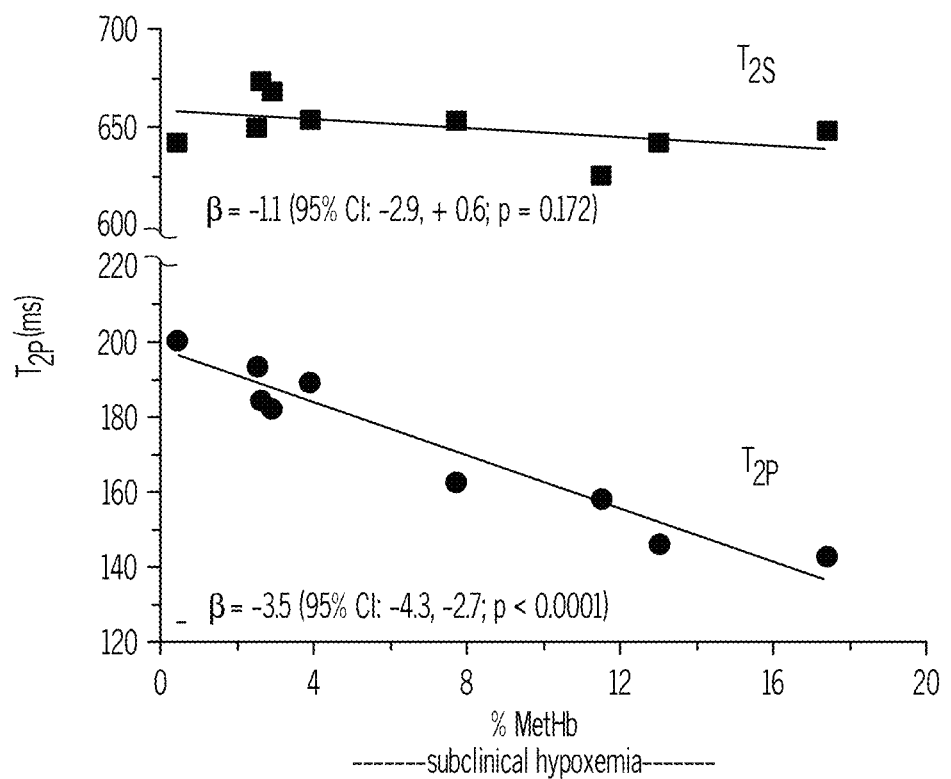
FIG. 12 shows results from an ex vivo experiment where a sample of whole human blood was titrated with aqueous sodium nitrite, a pro-oxidant. Here, $T_{2P}$ decreased with increasing amounts of oxidized hemoglobin (% MetHb). Percent MetHb was measured using a blood gas analyzer. By contrast, $T_{2S}$ measured in the same sample did not change with % MetHb. The slope (beta) of the linear least squares regression line for $T_{2P}$ was statistically different from zero ($p<0.0001$), whereas the slope for the $T_{2S}$ line was statistically indistinguishable from zero ($p=0.172$). Sodium nitrite is chemically related to nitric acid, the pro-oxidant naturally produced in the human body when blood insulin rises. In chronic hyperinsulinemia, nitric acid may be overproduced, leading to an increase in % Met Hb and a decrease in $T_{2P}$.

FIG. 12 shows the association between $T_{2P}$ and % MetHb in a whole blood sample titrated with sodium nitrite, a pro-oxidant. This compound increased hemoglobin oxidation, thereby increasing % Met Hb and decreasing $T_{2P}$. FIGS. 13A-13C show examples of benchtop, portable or miniaturized magnetic resonance relaxometry devices that can be used to measure $T_{2S}$ and $T_{2P}$ in whole blood.

In sum, settled whole blood yields two $T_2$ values: (1) $T_{2S}$, which represents plasma water $T_2$ after correcting for (Hct)[6]; and (2) $T_{2P}$, which monitors the oxygenation and oxidation state of Hb. Surprisingly, $T_{2P}$ was also correlated with markers of cardiometabolic health in apparently healthy adults. As such, $T_{2P}$ also links hemoglobin status to cardiometabolic health. Without being bound by theory, the causal mediation analysis supports the hypothesis that a lower $T_{2P}$ value likely represents a higher Met-Hb value, which mediates the association of hyperinsulinemia with hypoxia and chronic inflammation.

Example 1.8. Discussion

Human blood is a complex biofluid, and water protons are distributed in several microenvironments within blood, such as protons in the intracellular fluid and plasma, including water protons that are hydrogen-bonded to proteins and other molecules.

In settled anti-coagulated whole blood, at least two distinct water proton microenvironments can be resolved in the time domain, yielding two distinct $T_2$ values. The higher value is designated $T_{2S}$, as it arises from the plasma supernatant. The lower value is $T_{2P}$, as it arises from the blood cell pellet. The NMR signal intensity from a blood sample (e.g., a pellet of the blood sample) is predominately from red blood cells, as red blood cells outnumber white blood cells and platelets by approximately 1000 to 1. The most abundant source of protons (hydrogens) in red blood cells is water molecules, with smaller contributions from proteins, especially hemoglobin, and membrane lipids. Thus, $T_{2P}$ is predominately a measure of the $T_2$ relaxation time constant of water molecules inside red blood cells.

Oxygen-carrying hemoglobin is dissolved in the intracellular water of red blood cells. The water molecules bind to hemoglobin, generating an equilibrium between bound and unbound water, and a kinetic exchange of water on and off the protein. The observed $T_{2P}$ value arises from the weighted average of bound and unbound water, as the on/off exchange rate is fast compared with the $T_2$ time scale. Thus, water molecules are intimately associated with the concentrated hemoglobin inside red blood cells, and can sense changes in its oxygenation and oxidation state, as well as its concentration.

Hemoglobin that lacks bound oxygen (deoxy-hemoglobin or deoxy-Hb) is paramagnetic, as the unoccupied heme groups have unpaired electrons. The paramagnetic heme lowers the observed $T_{2P}$ value through a phenomenon called paramagnetic relaxation enhancement. By contrast, hemoglobin molecules with bound oxygen (oxy-hemoglobin or oxy-Hb) have no unpaired electrons, are not paramagnetic, and do not cause paramagnetic relaxation enhancement. The observed $T_{2P}$ value for oxy-hemoglobin is higher than that for deoxy-hemoglobin. In this manner, $T_{2P}$ is sensitive to the oxygenation state of reduced (functional) hemoglobin.

When hemoglobin becomes oxidized to form MetHb, it can no longer bind oxygen, but instead binds water molecules at the heme site where oxygen normally binds. Since MetHb is paramagnetic, the $T_{2P}$ is further lowered by paramagnetic relaxation enhancement, which is strengthened by the very close proximity of the water bound at the heme site. Thus, $T_{2P}$ is highly sensitive to the presence and amount of oxidized or MetHb as a percentage of total hemoglobin.

A preliminary ex vivo experiment with whole human blood supports proof-of-concept (FIG. 12). Samples of anticoagulated whole human blood from a healthy human subject were titrated with increasing amounts of 0.2% sodium nitrite, an oxidizing agent. Whole blood $T_{2P}$ was measured on each sample, and the state of the hemoglobin was measured using blood gas analysis. As the concentration of MetHb (as percent of total hemoglobin) increased from 0.4% (no sodium nitrite added) to 17.4% (40 µadded), the $T_{2P}$ value decreased in a linear fashion from 199.7±0.6 msec to 142.8±0.6 msec. Across the range of added sodium nitrite, the percentage of reduced, deoxy-hemoglobin remained low, <1%. Thus, the $T_{2P}$ value decreased with increasing amounts of MetHb in the blood, across the range expected for subclinical hypoxemia and subclinical methemoglobinemia in humans.

In principle, the NMR relaxation of the protons in different microenvironments gives rise to different $T_2$ relaxation constants as shown in equation 1.

$$I(t) = \sum_i A_i e^{-t/T_{2i}} \quad (1)$$

Here, I(t) is nuclear magnetic resonance (NMR) signal intensity, $A_i$ is signal amplitude and $T_{2i}$ is the transverse relaxation constant of ith proton microenvironment or mobility domain.

In mixed blood, red blood cells are suspended in the plasma, and water protons are in chemical exchange between the intracellular and extra-cellular compartments of mixed blood. The rate of chemical exchange is fast on the NMR $T_2$ time scale, giving rise to one observed $T_2$ component that is the weighted average between the two compartments. However, in settled blood, the water protons are not able to undergo fast chemical exchange between the two compartments because of the physical barriers created by the packed cells and the longer diffusion distance. This generates two distinct, slowly exchanging populations of water protons in the pellet and plasma supernatant. Therefore, settled blood, in contrast to mixed blood, gives two $T_2$ values, one each for plasma and cell pellet. In spectroscopy experiments, this phenomenon has also been reported to give rise to two separate NMR resonances for water protons in settled blood, implying slow exchange on the chemical shift time scale. Within the cell pellet, the protons in the intracellular and extracellular environments are in fast exchange, with the extracellular pool within the packed pellet being sparsely populated with water compared with the intracellular pool. This gives rise to only one observed $T_2$ for the pellet.

The paradoxical observation of strong correlations between $T_2$ and hematocrit, over the narrow range of hematocrit normally found in human blood, was puzzling at first. However, the in vitro generation of samples with artificially high hematocrit revealed the steep dependence shown in FIG. 6. In turn, the observed sixth power dependence on hematocrit pointed to paramagnetic relaxation enhancement (PRE) as the likely mechanism, as PRE has a theoretical six-power distance dependence.

Figure 5:
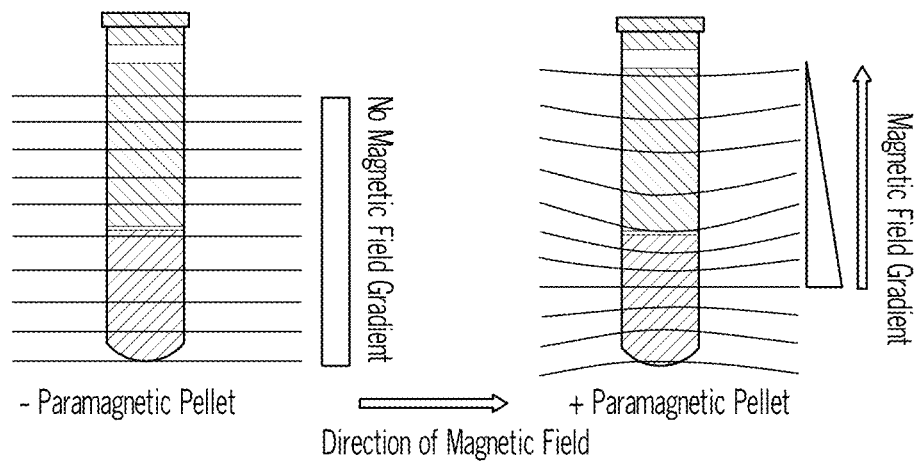
FIG. 5 shows magnetic field gradient formation in the presence of a paramagnetic pellet. Non-functional oxidized hemoglobin (methemoglobin) and reduced deoxy-hemoglobin contain unpaired electrons and thus, are paramagnetic. Reduced oxy-hemoglobin, the functional form in arterial blood that delivers oxygen to tissues, is not paramagnetic. Horizontal lines are magnetic field lines.

Hemoglobin exists in the oxygenated and deoxygenated forms, with the former being diamagnetic, and the latter, paramagnetic. Hemoglobin in blood exposed to room air includes a small percentage of deoxy hemoglobin and hence, is paramagnetic. By contrast, the plasma supernatant is essentially diamagnetic. As illustrated in FIG. 5, this difference creates a magnetic susceptibility gradient between the pellet and supernatant, which falls off as the sixth power of the distance from the pellet. As the hematocrit increases, the height of the supernatant becomes smaller, and the average distance between the rapidly diffusing water molecules in the supernatant and the pellet becomes smaller. Hence, water molecules in a short supernatant experience more of the magnetic susceptibility gradient. This gradient results in greater paramagnetic relaxation enhancement and shorter $T_{2S}$ values at higher hematocrit. In practice, the PRE effect can be exploited to assess hematocrit and red blood cell count in $T_2$ measurements of settled whole blood.

In contrast, the pellet $T_{2P}$ did not show the expected correlations with hematocrit and red blood cell count but revealed strong correlations with markers of insulin resistance/hyperinsulinemia, inflammation, dyslipidemia, oxidative stress and cellular damage (i.e., the pathophysiology of metabolic syndrome). This observation establishes a linkage between hemoglobin status (measured by $T_{2P}$) and metabolic health. Without being bound by theory, Applicant hypothesizes that $T_{2P}$ is detecting subclinical hypoxemia and possible tissue hypoxia.

The strong correlations of $T_{2S}$ with metabolic biomarkers, as shown in Table 2, indicate that settled whole blood is surprisingly informative and provides a practical sample format for assessing metabolic health by NMR relaxometry. Small amounts of whole blood can be obtained by fingerstick or armstick, without the need for phlebotomy and centrifugation, which opens up the possibility of performing whole blood NMR relaxometry in point-of-care settings such as clinics.

In sum, this Example describes a method for detecting hypoxemia, such as in situations where hypoxemia is least expected (e.g., in asymptomatic, apparently healthy individuals). The method records the spin-spin relaxation time constant of the cell pellet ($T_{2P}$) in a sample of settled, anti-coagulated whole human blood. The measurement is made using a compact tabletop magnetic resonance relaxometry device. The small blood sample can be obtained using conventional venipuncture or from a fingerstick drop. Whole blood $T_{2P}$ reports on the oxygenation and oxidation state of hemoglobin, a key protein inside red blood cells that delivers oxygen from the lungs to vital organs and tissues.

A low $T_{2P}$ value in an otherwise healthy individual points to a hidden impairment that could slowly and insidiously deprive cells of oxygen, resulting in cell and tissue damage. Specific examples could include slow damage to the oxygen-dependent insulin-secreting beta cells of the pancreas, leading to type 2 diabetes, or the cells lining the interior wall of arteries, leading to cardiovascular disease. Whole blood $T_{2P}$ overcomes the limitations of pulse oximetry and the impracticality of blood gas analysis for routine health screening and monitoring. It addresses an unmet need for better tools for the early detection of hidden health conditions in order to prevent diabetes, prediabetes, cardiovascular disease, metabolic syndrome and related conditions.

In a recent study of 44 asymptomatic, generally healthy adults, Applicant observed that $T_{2P}$ values varied over a surprisingly wide range, indicating varying degrees of hemoglobin oxygen binding and/or oxidation. Moreover, the low $T_{2P}$ values were associated with elevated markers of insulin resistance/hyperinsulinemia, inflammation, oxidative stress and cellular damage. For the first time, this discovery links hemoglobin status with metabolic health. Whole blood $T_{2P}$ solves the problem of undetected subclinical hypoxemia and gives clinicians an innovative new tool for early detection and disease prevention.

Whole blood $T_{2P}$ uses a different approach for probing the status of hemoglobin distinct from pulse oximetry and blood gas analysis. Whole blood $T_{2P}$ directly monitors the interior of red blood cells, which contain a highly concentrated aqueous solution of hemoglobin. Whole blood $T_{2P}$ monitors the hydrogen nuclei in the abundant water molecules, as well as those in the Hb. $T_{2P}$ can readily detect the difference between oxy-hemoglobin (hemoglobin saturated with bound oxygen) and deoxy-hemoglobin (hemoglobin without bound oxygen). Deoxy-Hb is paramagnetic, whereas oxy-Hb is not. The paramagnetism lowers the $^1$H $T_{2P}$ value through a process known as paramagnetic relaxation enhancement. Likewise, $T_{2P}$ can detect the difference between oxidized MetHb and non-oxidized oxy-Hb, as only the former is paramagnetic. Since MetHb binds water, not oxygen, the key probe of hemoglobin status is located right at the site of the oxidized heme group. Paramagnetic relaxation enhancement is maximized when the $^1$H probe is closest to the paramagnetic center.

Thus, whole blood $T_{2P}$ responds in a sensitive manner to changes in the amount of MetHb inside red blood cells. The measured $T_{2P}$ reflects the combined presence of deoxy-Hb and MetHb: the lower the $T_{2P}$, the higher the levels of deoxy-Hb and/or MetHb. As both forms of hemoglobin decrease the delivery of oxygen to tissues, whole blood $T_{2P}$ can detect subclinical hypoxemia that is missed by conventional pulse oximetry.

Another novel element of this method is that the measurement is made in a small volume of settled whole human blood. Therefore, the blood cells need not be separated from the liquid plasma, making this method practical for point-of-care analysis, as well as for conventional clinical lab analysis of blood samples obtained using venipuncture. Finally, this technology includes a novel table-top magnetic resonance device optimized for measuring whole blood $T_{2P}$.

$T_{2P}$ can be measured using existing relaxometry devices, even though they were not designed nor optimized for this purpose. Currently, Applicant is using a Bruker mq20 relaxometer to measure $T_{2P}$ in blood. In particular, Applicant is using a Bruker mq20 relaxometer to measure $T_{2P}$ in a 40 microliter sample of settled whole blood. The sample has an upper plasma supernatant and lower cell pellet. The sample is contained in a 3 mm-diameter coaxial insert housed within an empty 10 mm outer tube. The magnet air gap, probe size and instrument are much larger than needed, and the experiment is less efficient than it would be using a device optimized for this purpose.

To date, Applicant has established correlations between $T_{2P}$ and over 120 markers of human health status in 44 individuals. These results established that $T_{2P}$ can be measured in whole human blood and established the linkage between hemoglobin status ($T_{2P}$) and metabolic health.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of detecting hypoxemia in a subject, said method comprising:
  receiving a blood sample from the subject;
  measuring the $T_2$ relaxation time constant of the blood cells of the blood sample ($T_{2P}$ value), wherein the $T_{2P}$ value represents the spin-spin relaxation time constant of the blood cell component of the blood sample, wherein the blood cell component is in the form of a pellet, and wherein the $T_{2P}$ value is represented by the following formula:

$$I(t) = \sum_i A_i e^{-t/T_{2i}}$$

wherein I(t) represents the nuclear magnetic resonance (NMR) signal intensity, $A_i$ represents the signal amplitude, and $T_{2i}$ represents the transverse relaxation time constant of ith proton microenvironment or mobility domain; and
  correlating the measured $T_{2P}$ value to hypoxemia.

2. The method of claim 1, wherein the blood cell component is in the form of a pellet of an anti-coagulated whole blood sample.

3. The method of claim 1, wherein the correlating comprises correlating a lower-than-average $T_{2P}$ value to hypoxemia.

4. The method of claim 3, wherein the lower-than-average $T_{2P}$ value is attributed to elevated levels of deoxy hemoglobin (deoxy-Hb), elevated levels of oxidized hemoglobin (MetHb), or combinations thereof.

5. The method of claim 1, further comprising a step of correlating the measured $T_{2P}$ value to the subject's susceptibility to one or more hypoxemia-related conditions.

6. The method of claim 5, wherein the one or more hypoxemia-related conditions is selected from the group consisting of hypoxia, cellular damage, tissue damage, type 2 diabetes, cardiovascular disease, hyperinsulinemia, insulin resistance, inflammation, oxidative stress, dyslipidemia, hyperglycemia, early metabolic imbalance, prediabetes, metabolic syndrome, adiposity, or combinations thereof.

7. The method of claim 5, wherein a lower-than-average $T_{2P}$ value is correlated to the subject's susceptibility to one or more hypoxemia-related conditions.

8. The method of claim 1, further comprising a step of making a treatment decision.

9. The method of claim 8, wherein the treatment decision comprises monitoring the subject for signs or symptoms of hypoxemia, administering a therapeutic agent to the subject, or combinations thereof.

10. The method of claim 8, wherein the method further comprises implementing the treatment decision.

11. The method of claim 8, wherein the method is repeated after implementing the treatment decision.

12. The method of claim 1, wherein the subject is a human being.

13. The method of claim 1, wherein the subject shows no hypoxemia-related symptoms.

14. The method of claim 1, wherein the method occurs manually.

15. The method of claim 1, wherein the method occurs through the utilization of a computer program.

16. A system for detecting hypoxemia in a subject, wherein the system comprises one or more computer-readable storage mediums having a program code embodied therewith, wherein the program code comprises programming instructions for:
  receiving a blood sample from the subject;
  measuring the $T_2$ relaxation time constant of blood cells of the blood sample ($T_{2P}$ value), wherein the $T_{2P}$ value represents the spin-spin relaxation time constant of the blood cell component of the blood sample, wherein the blood cell component is in the form of a pellet, and wherein the $T_{2P}$ value is represented by the following formula:

$$I(t) = \sum_i A_i e^{-t/T_{2i}}$$

wherein I(t) represents the nuclear magnetic resonance (NMR) signal intensity, $A_i$ represents the signal amplitude, and $T_{2i}$ represents the transverse relaxation time constant of ith proton microenvironment or mobility domain; and
  correlating the measured $T_{2P}$ value to hypoxemia.

17. The system of claim 16, wherein the programming instructions correlate a lower-than-average $T_{2P}$ value to hypoxemia.

18. The system of claim 16, wherein the system further comprises programming instructions for correlating the measured $T_{2P}$ value to the subject's susceptibility to one or more hypoxemia-related conditions.

19. The system of claim 18, wherein the programming instructions correlate a lower-than-average $T_{2P}$ value to the subject's susceptibility to one or more hypoxemia-related conditions.

20. The system of claim 16, wherein the system further comprises programming instructions for recommending a treatment decision.

21. The system of claim 16, wherein the system is in the form of a web-based program, an application-based program, or combinations thereof.

* * * * *